(12) United States Patent
Brunson et al.

(10) Patent No.: US 10,463,531 B2
(45) Date of Patent: Nov. 5, 2019

(54) IONTOPHORESIS MASSAGER

(71) Applicant: L'OREAL, Paris (FR)

(72) Inventors: Kaye Brunson, Woodinville, WA (US);
Lilac Muller, Woodinville, WA (US);
Zane Bowman Allen Miller, Seattle, WA (US); Vincenzo Casasanta, III, Woodinville, WA (US)

(73) Assignee: L'OREAL, Paris (FR)

( * ) Notice: Subject to any disclaimer, the term of this patent is extended or adjusted under 35 U.S.C. 154(b) by 834 days.

(21) Appl. No.: 14/984,133

(22) Filed: Dec. 30, 2015

(65) Prior Publication Data
US 2017/0189227 A1 Jul. 6, 2017

(51) Int. Cl.
*A61H 23/00* (2006.01)
*A61N 1/30* (2006.01)
*A61F 7/00* (2006.01)
*A61N 5/06* (2006.01)
*A61N 1/04* (2006.01)
(Continued)

(52) U.S. Cl.
CPC ........... *A61F 7/007* (2013.01); *A61H 23/004* (2013.01); *A61N 1/0428* (2013.01); *A61N 1/303* (2013.01); *A61N 1/325* (2013.01); *A61N 1/36021* (2013.01); *A61N 5/0625* (2013.01); *A61F 2007/0087* (2013.01); *A61H 2201/0157* (2013.01); *A61H 2201/10* (2013.01); *A61N 2005/0644* (2013.01); *A61N 2005/0659* (2013.01)

(58) Field of Classification Search
CPC ............. A61F 7/007; A61F 2007/0087; A61N 5/0625; A61N 1/0428; A61N 1/303; A61N 1/325; A61N 1/36021; A61N 2005/0659; A61N 2005/0644; A61H 23/004; A61H 2201/10; A61H 2201/0157
See application file for complete search history.

(56) References Cited

U.S. PATENT DOCUMENTS

2004/0220622 A1* 11/2004 Bernabei ................. A61H 7/008
607/3
2005/0113725 A1* 5/2005 Masuda .............. A61H 23/0263
601/72
(Continued)

*Primary Examiner* — Quang D Thanh
(74) *Attorney, Agent, or Firm* — Oblon, McClelland, Maier & Neustadt, L.L.P.

(57) ABSTRACT

A system is provided for stimulating a portion of skin, the system including at least two electrodes; a motor and an electrical system, the electrical system including a power source; and an end effector operably coupled to the motor and the electrical system, the end effector having at least one embedded electrode, from the at least two electrodes, disposed and operably coupled to the electrical system at which the end effector is configured to be in electrical communication with the portion of skin, wherein the motor is configured to subject the end effector to repetitive movements while contacting the skin to provide mechanical stimulation to the skin, wherein the at least one embedded electrode is configured to serve as a source electrode and another of the at least two electrodes is configured to serve as a return electrode, and wherein the power source is configured to bias the source electrode to the return electrode and form an electric field with the portion of skin.

14 Claims, 21 Drawing Sheets

(51) Int. Cl.
*A61N 1/32* (2006.01)
*A61N 1/36* (2006.01)

(56) References Cited

U.S. PATENT DOCUMENTS

| | | | | |
|---|---|---|---|---|
| 2005/0251242 A1* | 11/2005 | Bousfield | ............... | A61N 1/322 |
| | | | | 607/150 |
| 2009/0171313 A1* | 7/2009 | Yamamoto | ............. | A61N 1/044 |
| | | | | 604/501 |
| 2013/0158547 A1* | 6/2013 | David | ................... | A61B 18/14 |
| | | | | 606/41 |
| 2014/0142472 A1* | 5/2014 | Giraud | .................. | A61H 7/005 |
| | | | | 601/18 |
| 2014/0378555 A1* | 12/2014 | Hung | ....................... | A61N 1/30 |
| | | | | 514/773 |
| 2015/0088050 A1* | 3/2015 | Chang | ................... | A61N 1/328 |
| | | | | 604/20 |
| 2015/0305969 A1* | 10/2015 | Giraud | .................. | A61H 7/005 |
| | | | | 601/18 |

\* cited by examiner

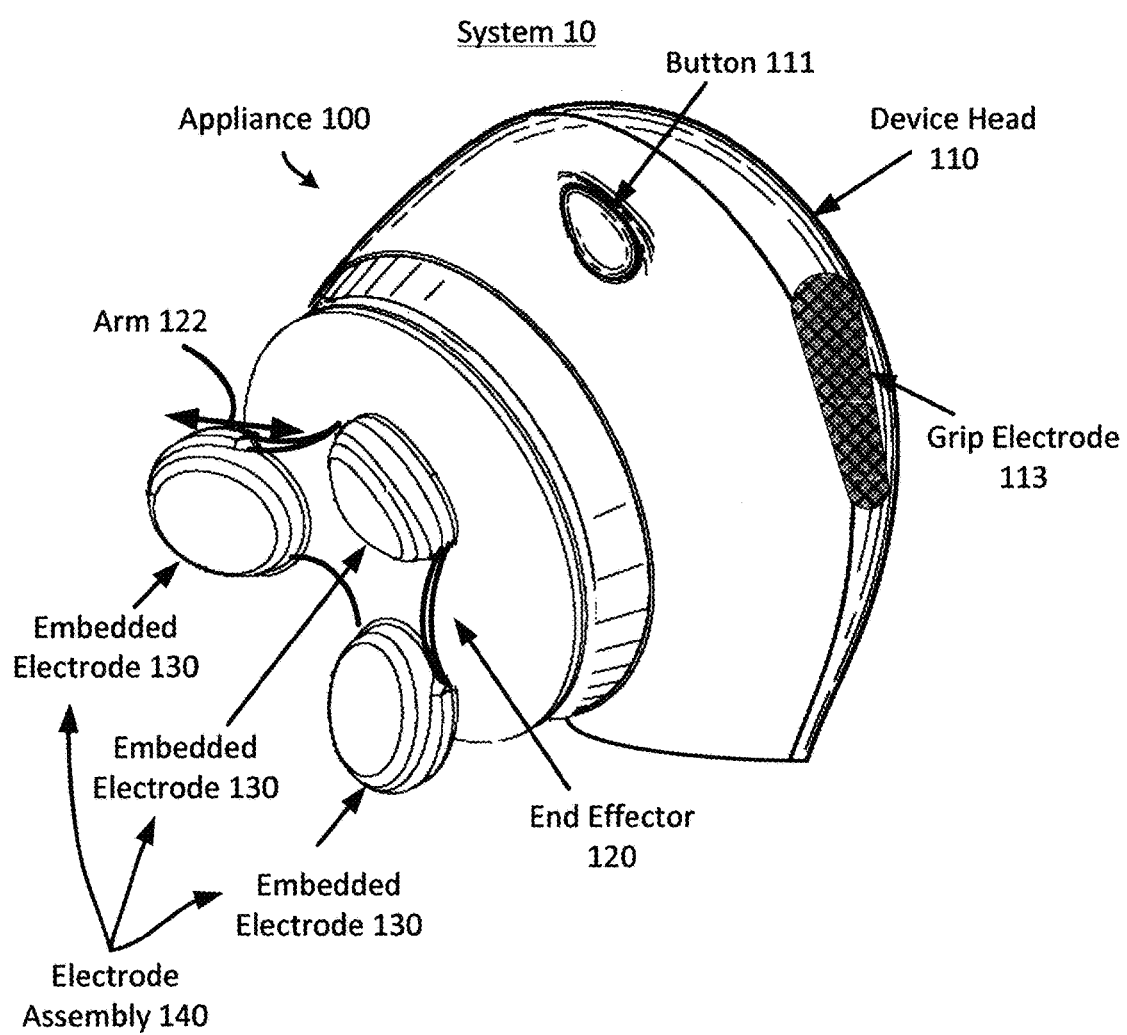

System 10

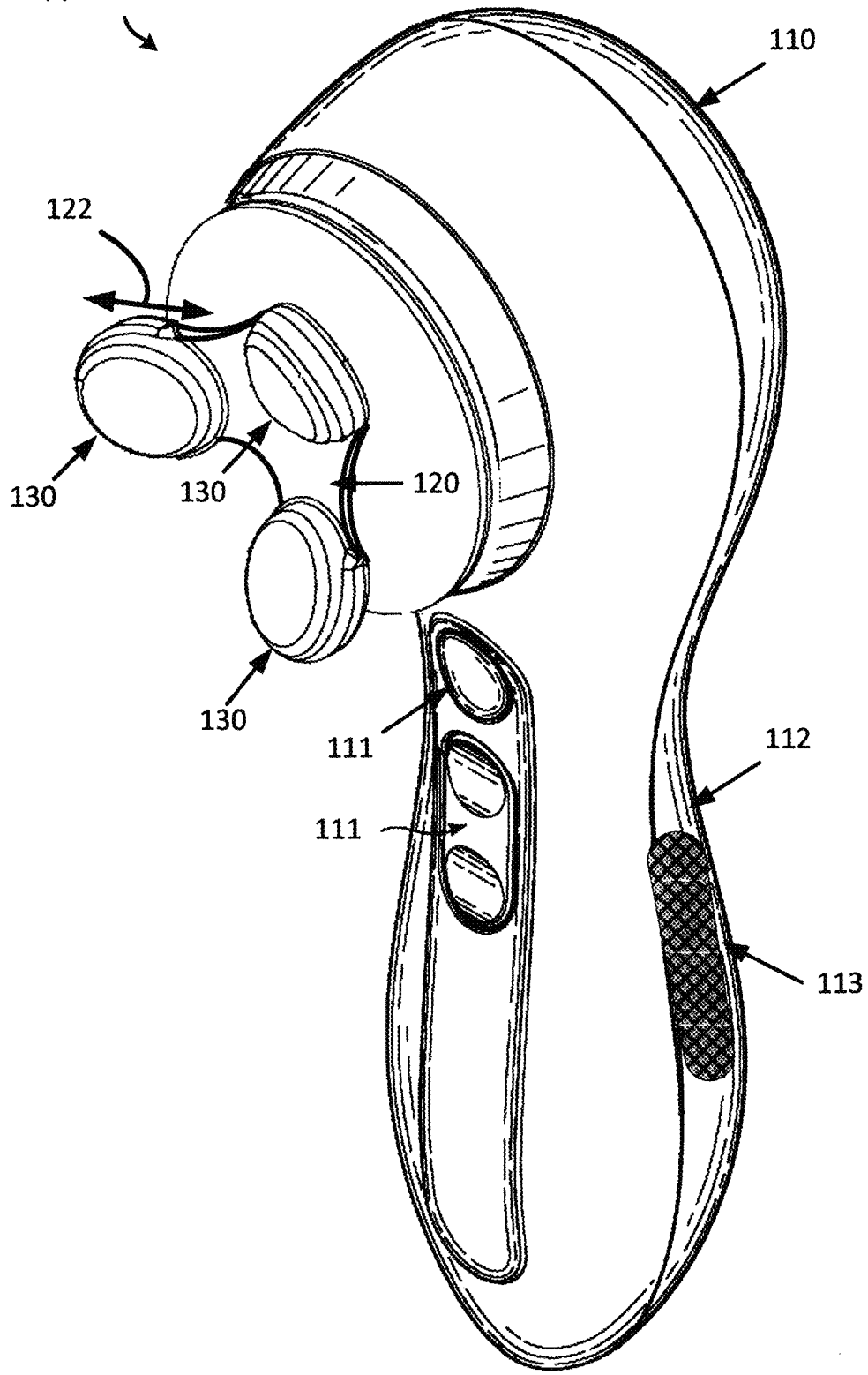

Electrical Circuit A

Electrical Circuit B

System 10

Embedded Electrode 130

Embedded Electrode surface showing the Electrode Contact Layer

Embedded Electrode surface showing an indicator sign

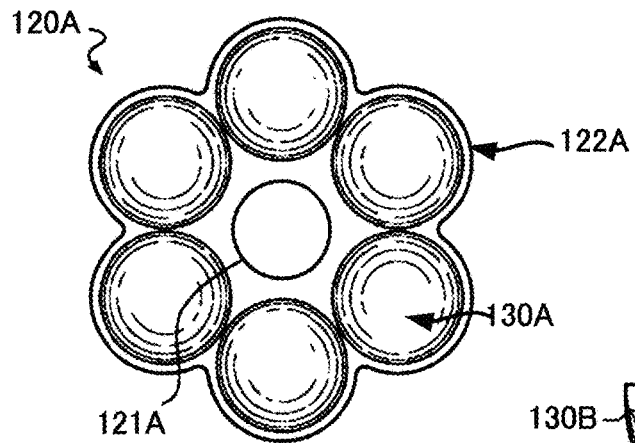
FIG. 8A
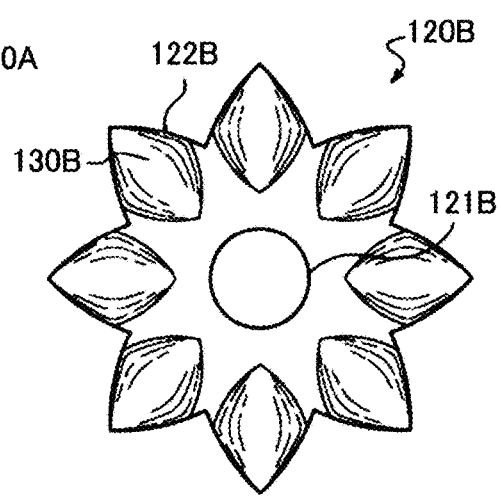
FIG. 8B
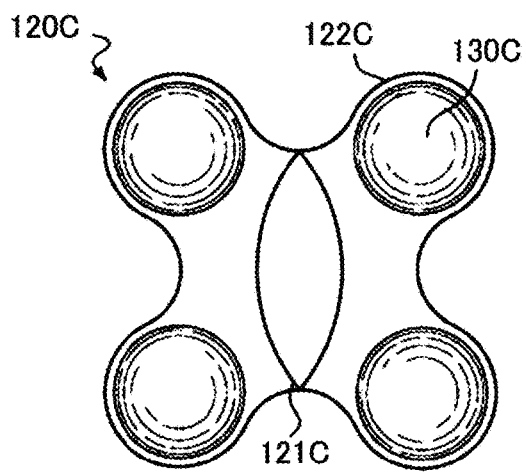
FIG. 8C
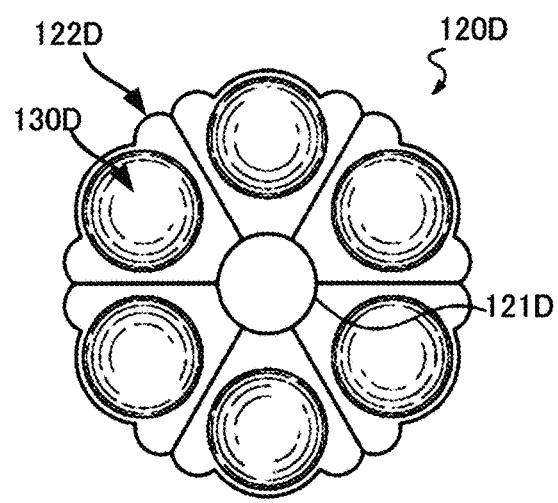
FIG. 8D
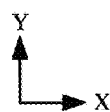

Adjustable End Effector configured to change the spatial distribution of the Electrode Assembly

Change in the End Effector position relative to the skin

IONTOPHORESIS MASSAGER

BACKGROUND

Field

The present application is directed to a method and system of using electrodes to provide a stimulus to the skin surface of the user using iontophoresis.

SUMMARY

In an embodiment, a system is provided for stimulating a portion of skin, the system including: at least two electrodes; a motor and an electrical system, the electrical system including a power source; and an end effector operably coupled to the motor and the electrical system, the end effector having at least one embedded electrode, from the at least two electrodes, disposed and operably coupled to the electrical system at which the end effector is configured to be in electrical communication with the portion of skin, wherein the motor is configured to subject the end effector to repetitive movements while contacting the skin to provide mechanical stimulation to the skin, wherein the at least one embedded electrode is configured to serve as a source electrode and another of the at least two electrodes is configured to serve as a return electrode, wherein the power source is configured to bias the source electrode to the return electrode and form an electric field with the portion of skin.

In an embodiment, the end effector further includes a set of contact points that are located at a target distance from each other that is based on an inverse of a target motion frequency.

In an embodiment, the embedded electrodes or contact points are located at a target distance from each other that is based on an inverse of a target motion frequency, wherein the motor is configured to move the end effector such that, when the motor is operating, the motor and end effector have a resonant frequency based on the target motion frequency, wherein, when the motor is operating and a force is applied to the system to bias the end effector toward the portion of skin, the end effector produces a cyclical stimulus within the portion of skin at about the target motion frequency.

In an embodiment, the power source is configured to form an electric field that performs iontophoresis in the portion of skin.

In an embodiment, a formulation is used during iontophoresis that includes one or more of a cosmetic composition, a medical ointment, a cleanser, or any other composition that is capable of being applied to a portion of skin.

In an embodiment, the power supply is configured to form an electric field that creates a microcurrent in the portion of skin.

In an embodiment, a heating element is provided that is configured to radiate heat to the portion of skin.

In an embodiment, the embedded electrode is connected to the end effector via a flexible arm.

In an embodiment, the return electrode is disposed in a handle of the system configured to be gripped by a user's hand.

In an embodiment, the return electrode is another embedded electrode included as part of the end effector.

In another embodiment, a method is provided, implemented by a system for stimulating a portion of skin, the system including at least two electrodes, a motor, an electrical system that includes a power source; and an end effector operably coupled to the motor and the electrical system, the end effector having at least one embedded electrode, from the at least two electrodes, disposed and operably coupled to the electrical system at which the end effector is configured to be in electrical communication with the portion of skin, the method including: subjecting the end effector to repetitive movements while contacting the skin to provide mechanical stimulation to the skin, wherein the at least one embedded electrode is configured to serve as a source electrode and another of the at least two electrodes is configured to serve as a return electrode; and biasing, by the power source, the source electrode to the return electrode and form an electric field with the portion of skin.

In an embodiment, wherein the end effector further includes a set of contact points that are located at a target distance from each other that is based on an inverse of a target motion frequency, the embedded electrodes or contact points are located at a target distance from each other that is based on an inverse of a target motion frequency, the method further includes moving the end effector such that, when the motor is operating, the motor and end effector have a resonant frequency based on the target motion frequency, wherein, when the motor is operating and a force is applied to the system, biasing the end effector toward the portion of skin, the end effector producing a cyclical stimulus within the portion of skin at about the target motion frequency.

In an embodiment, the method further includes forming an electric field that performs iontophoresis in the portion of skin.

In an embodiment, the method further includes forming an electric field that creates a microcurrent in the portion of skin.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A-1F schematically illustrate representative systems including an appliance having a device head, an end effector and a set of embedded electrodes in accordance with the disclosed embodiments;

FIGS. 8A through 8D depict top views of different embodiments of the end effectors;

DETAILED DESCRIPTION

Figure 1A:
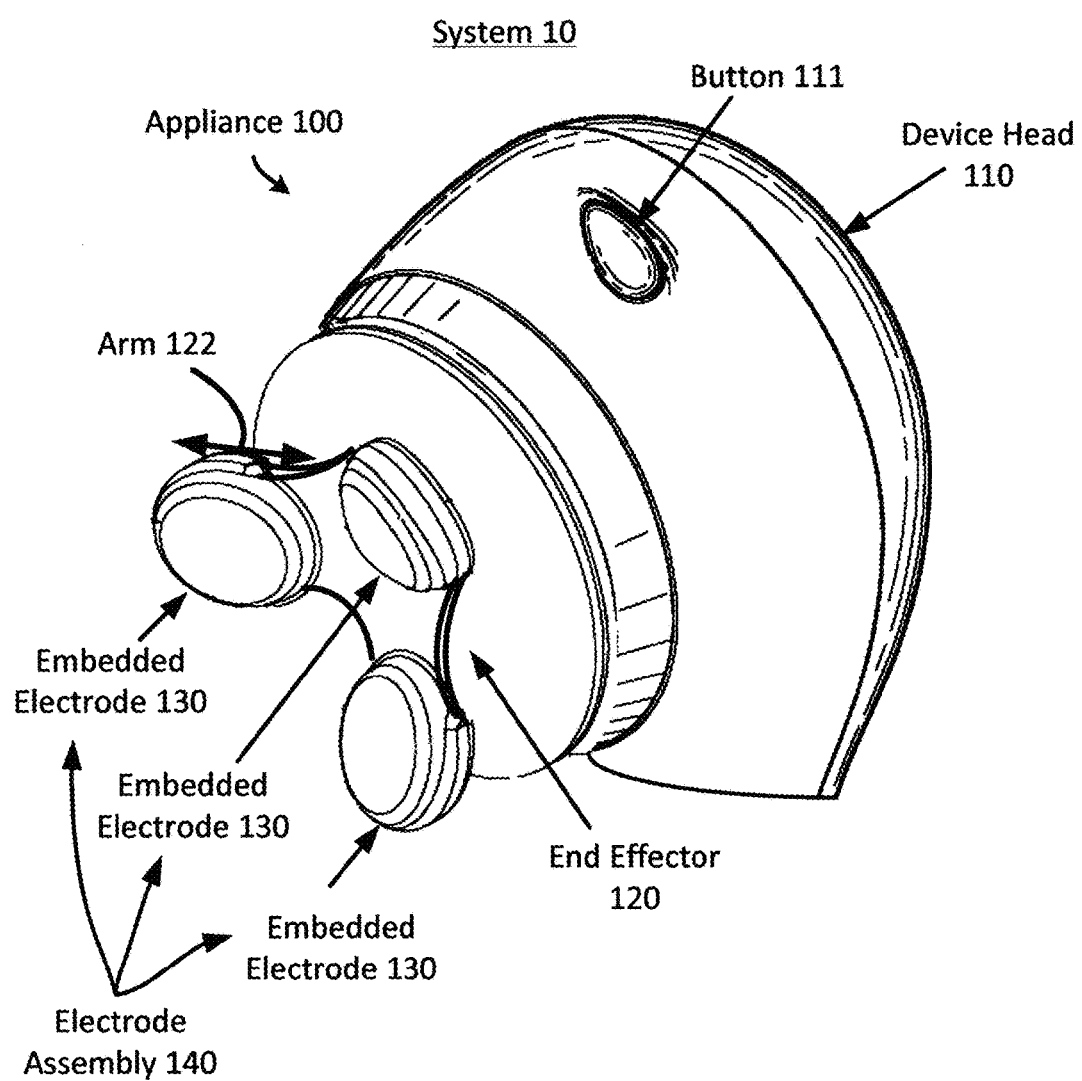

The present disclosure describes systems, methods, and related devices to provide techniques for leveraging multiple anti-aging modalities. The described systems, methods, and devices aim to create a unique consumer experience that leverages multiple anti-aging modalities including mechanical energy input by massage, infusion of actives and removal of impurities by iontophoresis, electrotherapy by microcurrents, and heat therapy. In an embodiment, diagnostics are provided to assess a property of the subject's skin, as well as to monitor the related devices for optimal operability.

There are multiple individual methods, materials, and systems for leveraging anti-aging modalities including that of delivering an active formulation using iontophoresis. A combination of one or more techniques can produce an enhanced therapeutic effect, as well as an increased comfort experience of a subject in comparison with any technique individually.

The methods, materials, and systems surrounding iontophoresis are described in an extensive literature with much of the physical/chemical analysis and development reported in the 1980's and 90's. Since that period these methods have been refined and perfected such that detailed iontophoresis prescriptions can be made for percutaneous infusion of a wide variety of formulations and molecules ranging from small molecule metabolites to large proteins on the scale of cytochrome C. A composition and orientation of a set of electrodes used in iontophoresis can have a substantial effect on the net outcome of the infusion for a given active ingredient, as well as a subject's experience of comfort.

In any electrochemical system where any two electrodes are biased as anode and cathode when in contact to a common electrolyte; oxidation and reduction will most likely occur. This effect is commonly observed for iontophoresis applications using inert or passivated electrodes such as stainless steel, graphite, platinum (Pt) or gold (Au). In such cases, a runaway pH change may cause mild to severe skin irritation, inhibit drifting of cations or anions into an epidermis layer of the skin due to altering of the skin's conductivity and permeability, as well as degrade the formulation.

Current methods, materials, and systems for providing active therapeutic agents to a subject's skin using iontophoresis do not provide conditions for both an optimal therapeutic effect and a comfort experience of the subject. Since much variability can exist with any potential iontophoresis electrode and active formulation combination, it will be advantageous to have a platform whereby any given active formulation will also make provision for an appropriate electrode combination. A consumable formulation-specific electrode is disclosed that presents an electrochemically appropriate surface to an iontophoresis application treatment area with respect to an electric circuit contact (e.g. hand, wrist, adjacent areas, etc.) and an accompanying active formulation. The formulation-specific electrode involves a low cost and disposable plastic electrode base that is finished with a thin layer of electrochemically compatible metal, salt, compound, or polymer. Used in conjunction with an iontophoresis capable device, the formulation-specific electrode will provide a surface to create optimal treatment conditions including voltage/current profiles for the active formulation having any given molecular weight, buffer composition, and ionization state.

This disclosure also relates to a set of methods, materials, and systems for leveraging multiple anti-aging techniques to produce an enhanced therapeutic effect, as well as an increased comfort experience of a subject in comparison with any technique individually. One such technique is delivery of an active formulation by iontophoresis. Since much variability can exist with any potential iontophoresis electrode and active formulation combination, it will be advantageous to have a platform whereby any given active formulation will also make provision for an appropriate electrode having an electrochemically appropriate surface. An iontophoresis massager device is disclosed to deliver the active formulation in conjunction with a set of formulation-specific electrodes. Used in conjunction with the formulation-specific electrodes, the iontophoresis massager can provide optimal treatment conditions including voltage/current profiles for the active formulation having any given molecular weight, buffer composition, and ionization state.

The disclosed embodiments include a handheld personal appliance or appliance that can be configured to concurrently or sequentially operate in one or more function modes including a massage mode, an iontophoresis mode, a microcurrent mode, a heat delivery mode, and a diagnostic mode, and can operate in single or multi-mode modality.

The massage mode can be configured to deliver a massage or mechanical stimuli designed to increase cellular production of specific proteins and aid in relaxation of a user or subject. The iontophoresis mode can enable infusion of actives in the presence of an applied electrical field. In another example, the iontophoresis mode can enable removal of impurities in the presence of an applied electrical field. The microcurrent mode can be configured to enable electrotherapy including cosmetic electrotherapy such as muscle toning, micro-lifting, etc. The heat therapy mode can be configured to provide heat therapy, to enhance the infusion of actives or the removal of impurities, and to deliver a pleasurable experience. The diagnostic mode can be configured to sense a property or parameter of the subject's skin.

The appliance can be used in conjunction with one or more formulations for enhancing a single or a combination mode or for providing an anti-aging treatment, such as mechanically stimulating the skin and increasing the penetration rate or flux of cosmetic or therapeutic molecules to an epidermis layer of the skin.

Mechanobiology

Various forms of energy input into biological organisms have different effects on the biological organisms. These forms of energy input include mechanical inputs, thermal inputs, electromagnetic inputs, electrical inputs, acoustic inputs, and the like. One particular field of study, known as mechanobiology, aims to understand how physical forces and changes in cell or tissue mechanics affect biological organisms.

Under certain conditions, mechanical stimuli (e.g., applied cyclical strain, mechanical motion, applied strain, and the like) input to a portion of skin of a biological organism causes an increase in biomarker (e.g., protein) production. In one example, a number of proteins within the skin can be regulated using, among other things, cyclical mechanical strain applied at particular frequencies using an end effector.

The massage mode can be configured to deliver a massage or mechanobiology stimuli and aid in relaxation of a user or subject. The disclosed embodiments employ technologies and methodologies that stimulate frequency response of cells in the dermis and epidermis to induce production of proteins associated with young, healthy skin.

Human skin cells (dermal fibroblasts in particular) respond to strain in tissue with cytoskeletal reordering and increased production in extracellular matrix proteins.

In an embodiment, by combining discrete, differential strain in the skin at specific frequencies, the disclosed technologies and methodologies induce increased growth and repair activities from multiple cell types found in the skin, thereby producing an anti-aging effect.

Depending on the particular location of the portion of skin in a biological organism, mechanical motion or strain generated in a range from about 60 Hz to about 120 Hz may stimulate anti-aging effects.

In an embodiment, the cumulative effects of applying cyclical mechanical strain as disclosed include one or more anti-aging effects. For example, by applying a particular stress to the skin, cutaneous cells will react to the stress by upregulating (increasing) production of certain proteins. The character and duration of the stress will affect which proteins are upregulated and to what extent.

As a non-limiting example of the benefits achievable, certain disclosed embodiments can be used to upregulate the production of integrin in the skin, which results in anti-aging effects by increasing epidermal cohesion.

The following discussion provides examples of systems, apparatuses, and methods for implementing technologies and methodologies for mechanically stimulating a portion of skin at a motion frequency in order to improve skin health through upregulating production of certain proteins within the portion of skin.

In one embodiment, a system for mechanically stimulating a portion of skin at a motion frequency includes an appliance having a motor and an end effector operably coupled to the motor. The end effector includes a plurality of embedded electrodes at which the end effector is configured to contact the portion of skin. The plurality of embedded electrodes are located at a target distance from each other that is based on an inverse of a target motion frequency. The motor is configured to move the end effector such that, when the motor is operating, the system has a resonant frequency based on the target motion frequency. When the motor is operating and a force is applied to the system to bias the end effector toward the portion of skin, the end effector produces a cyclical stimulus within the portion of skin at about the target motion frequency.

In one example, the end effector includes a cup-shaped end configured such that the plurality of embedded electrodes are the only portions of the end effector to contact the portion of skin when the force is applied from the end effector to the portion of skin. In another example, the motor is configured to impart one or more of oscillatory motion, vibrational motion, or cyclical mechanical strain to the end effector. In another example, the end effector includes a central portion and an plurality of arms. In another example, the central portion has a mass selected such that the system has the resonant frequency when the motor is operating.

In another example, the plurality of arms includes the plurality of embedded electrodes, and wherein the arm is connected to the central portion via a central support such that the plurality of embedded electrodes are cantilevered away from the central support. In another example, the end effector is releasably couplable to the appliance, the end effector includes a drive assembly that engages a drive hub of the appliance when the end effector is releasably coupled to the appliance, and the motor is operatively coupled to the drive hub such that operation of the motor causes movement of the drive hub that is transferred to the drive assembly to move the end effector.

In another embodiment, an end effector for mechanically stimulating a portion of skin at a motion frequency includes a central portion that is couplable to a motor and an plurality of arms having a plurality of embedded electrodes at which the end effector is configured to contact the portion of skin. The plurality of embedded electrodes are located at a target distance from each other that is based on an inverse of the motion frequency. The end effector is configured such that, when the central portion is coupled to the motor and the motor is operating, the end effector has a resonant frequency based on the motion frequency. When the motor is operating and a force is applied to bias the end effector toward the portion of skin, a cyclical stimulus is produced within the portion of skin at about the motion frequency.

In one example, the plurality of embedded electrodes includes at least three embedded electrodes arranged equidistantly from each other. In another example, a distance between each set of two of the three embedded electrodes is a whole increment of the inverse of the motion frequency. In another example, each of the plurality of embedded electrodes is located on one of a plurality of arms and edges of each of the plurality of arms has a rounded shoulder. In another example, each of the plurality of arms has at least one of a rounded shoulder, at least one slit across a face of the arm, or surface texturing on a face. In another example, a surface of the end effector has a hardness in a range from about 10 Shore A to about 60 Shore A. In another embodiment, the end effector can include a dispenser configured to dispense a treatment composition to the portion of skin in response to the dispenser coming into contact with the portion of skin. In another example, the motion frequency is in a range from about 60 Hz to about 120 Hz. In another example, the force applied from the end effector to the portion of skin is in a range from about 85 grams-force to about 100 grams-force.

In another embodiment, a method of treating a portion of skin at a motion frequency using an appliance including a motor coupled to an end effector includes driving at a resonant frequency the end effector having a plurality of embedded electrodes located at a distance from each other that is based on an inverse of a target motion frequency and inducing a cyclical stimulus at about the target motion frequency within a portion of skin contacted by the plurality of embedded electrodes.

In one example, the method further includes applying a composition to the portion of skin using the end effector while driving the end effector at the resonant frequency. In another example, applying the composition includes applying a composition configured to treat a condition of the portion of skin. In another example, driving the end effector at the resonant frequency includes selecting the target motion frequency based on the condition of the portion of skin.

In an embodiment, an end effector with a plurality of embedded electrodes is used for mechanically stimulating a portion of skin at a motion frequency where the embedded electrodes are located a target distance from each other that is based on an inverse of the motion frequency.

In an embodiment, a system for mechanically stimulating a portion of skin at a motion frequency includes an appliance and an end effector with a plurality of embedded electrodes that are located a distance from each other that is based on an inverse of the motion frequency.

In an embodiment, a method for mechanically stimulating a portion of skin at a motion frequency includes activating operation of a motor to impart movement to an end of an end effector and applying a force to bias the end effector toward the portion of skin to cause a cyclical stimulus of the portion of skin at about the motion frequency. Examples of cyclical stimuli include cyclical mechanical strain induced in the portion of skin, cyclical pressure waves induced into the portion of skin, and the like.

Infusion of Actives

Anti-aging modalities can in part include use of an active ingredient, also referred to herein as an "active" or an "active molecule" or an "formulation", into the skin. In various embodiments, the formulations described herein are one or more of a cosmetic composition (e.g., makeup, foundation, bronzer, etc.), a medical ointment (e.g., antibacterial ointment, hydrocortisone cream, etc.), a cleanser (e.g., soap, makeup remover, etc.), or any other composition that is capable of being applied to a portion of skin. In various embodiments, the formulation is a liquid, a non-Newtonian substance, a gel, or any other type of composition. The formulation can be configured for uses such as skin care, skin cleansing, skin purification, skin exfoliation, skin desquamation, massage, cellulite, thinning, make up, and depigmentation.

Iontophoresis is a technique that uses a small electric charge to deliver charged species across a membrane, in most cases an agent through the skin. By creating an electric field between at least two electrodes contacting the skin, active transport of an ion (charged molecule) through the skin can be achieved. The ion in an appropriate formulation is repelled by the source electrode that carries the same charge as the ion, driving it through the stratum corneum and towards the return electrode. Many active ingredients in skin care have ionic forms, so iontophoresis can improve penetration of these ingredients into the epidermis.

Transcutaneous diffusion of molecules via iontophoresis is based on two principles, namely electrorepulsion and electroosmosis. Electrorepulsion is the migration of an ionized molecule by repulsion of charges of the same polarity. Thus, if a substance has a positive charge, it will diffuse through the skin at the anode (+). Electroosmosis is the migration of a molecule, even a non-ionized molecule, by entrainment associated with a flow of water from the anode to the cathode during iontophoresis. The migration is due in particular to the negative charge of the skin. Under the effect of a current, the water or a solvent entrains dissolved substances as it migrates.

The disclosed embodiments include a handheld personal appliance or appliance that can be configured to concurrently or sequentially operate in an iontophoresis mode. The iontophoresis mode can enable infusion of ionic actives in presence of an applied electrical field. In another example, the iontophoresis mode can enable removal of impurities in presence of an applied electrical field.

The composition of electrodes used in iontophoresis have been found to have substantial effect on the net outcome of percutaneous infusion for a given delivery load. In an aspect, the present disclosure seeks to address the primary problem of creating optimal conditions for matching electrode materials and voltage/current profiles to deliver an effective dose of the active ingredient into the skin. In order to address this use a product solution is described that accounts for the wide variability in formulations, electrodes, and voltage/current profiles.

In this case, the embodiments described below add new methods and related devices to the list of techniques for leveraging multiple anti-aging modalities, which when combined with a set of formulation-specific electrodes, can create optimal conditions for electrode materials and voltage/current profiles for the formulation with any given molecular weight, buffer composition, and ionization state.

Electrotherapy

The microcurrent mode can be configured to enable electrotherapy including cosmetic electrotherapy such as muscle toning, micro-lifting, etc. During electrotherapy, application of a sufficient microcurrent between two or more electrodes can cause tightening of the underlying muscle or the skin. In one example, the electrotherapy can evoke vasoconstriction, narrowing of the blood vessels, or vasodilation, expanding of the blood vessels. In another example, the microcurrent mode can work in conjunction with the heat therapy mode to enhance or counter act the vasoconstriction effect or the vasodilation effect.

In an embodiment, the microcurrent mode can also be configured for transcutaneous electrical nerve stimulation (TENS). For instance, for pain management or to induce muscle contractions as part of electrical muscle stimulation (EMS).

Heat Therapy

The heat therapy mode can be configured to provide heat therapy, to enhance the infusion of actives or the removal of impurities, and to deliver a pleasurable experience. Accordingly the appliance advantageously includes a source of heat or a heating element. The heating element to provide heat may include a heating resistor or a thermoelectric element or an infrared source. Preferably, the source of heat includes an infrared source or a resistor.

Diagnostic Modes

Any combination of the function modes and the formulations can be based on any electrodermal activity of the subject's skin. The electrodermal activity (EDA) is a property of the human body that causes continuous variation in the electrical characteristics of the skin. Examples of the EDA include skin conductance, galvanic skin response (GSR), electrodermal response (EDR), psychogalvanic reflex (PGR), skin conductance response (SCR), and skin conductance level (SCL).

In one aspect, the diagnostic mode can be configured to sense a property or parameter of the subject's skin including one of an electrical property, a mechanical property, an electro-mechanical property such as elasticity or tightness, and a surface contour property such as in quantifying wrinkle abundance or depth. In one example, the parameter of the skin can be one or more of the EDA properties of the skin.

In one embodiment the appliance can include memory where the diagnostic mode can store the sensed skin property before, during, or after the treatment for comparison or feedback. In one embodiment, the diagnostic mode can be configured to perform a scan similar to electrical impedance spectroscopy (EIS) and electrical impedance tomography (EIT) between the plurality of embedded electrode. In one aspect, the EIS or EIT scan can be used to identify the optimal parameters, to assess if further treatment will be beneficial, and to compare at least one property of the skin before and after the treatment.

In another aspect, the diagnostic mode can be configured to sense a property of the embedded electrode. In one aspect the diagnostic mode can be configured to sense a consumable electrode property such as a composition of a consumable electrode material or an effective remaining life of the composition.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein. Referring now to the drawings, wherein like reference numerals designate identical or corresponding parts throughout the several views.

FIGS. 1A-1F schematically illustrate representative systems including an appliance having a device head, an end effector and a set of embedded electrodes in accordance with the disclosed embodiments. FIG. 1A shows a first embodiment of a system 10 including the appliance 100 having a device head 110 connected to an end effector 120 having a central portion 121 and at least three arms 122 with an embedded electrode 130 disposed on each arm 122. An electrode assembly 140 describes a combination and spatial distribution of all of the embedded electrodes 130 on the end effector 120.

The end effector 120 can be flexible such that each arm 122 is configured to have its respective embedded electrode 130 be in electrical communication with a subject's skin. The appliance 100 can include one or more user input mechanisms or button 111, which can be used for controlling operations. In one embodiment, the device head 110 can further include a heating element (not shown) configured to generate and to deliver heat to the subject's skin. In another embodiment the end effector 120 can include the heating element. The heating element may include a heating resistor or a thermoelectric element or an infrared source. The device head 110 can further include other user interfacing features not shown such as a screen or an indicator for displaying an operating or function mode.

FIG. 1B shows a second embodiment of the appliance 100 where the device head 110 further includes a grip electrode 113 such that the grip electrode 113 is in contact or electrical communication with a separate location of the subject's skin simultaneously during operation from that of the other embedded electrodes 130. In this case, the grip electrode 113 can be positioned on the device head 110 having an ergonomic shape such that the grip electrode 113 is in contact with the subject's skin when the appliance 100 is held by the subject. According to different embodiments disclosed, either the grip electrode 113 or an embedded electrode 130 can be also used as a source electrode, a return electrode, a reference electrode, a ground electrode, or a counter electrode to complete an electrical circuit with the skin.

Figure 1C:
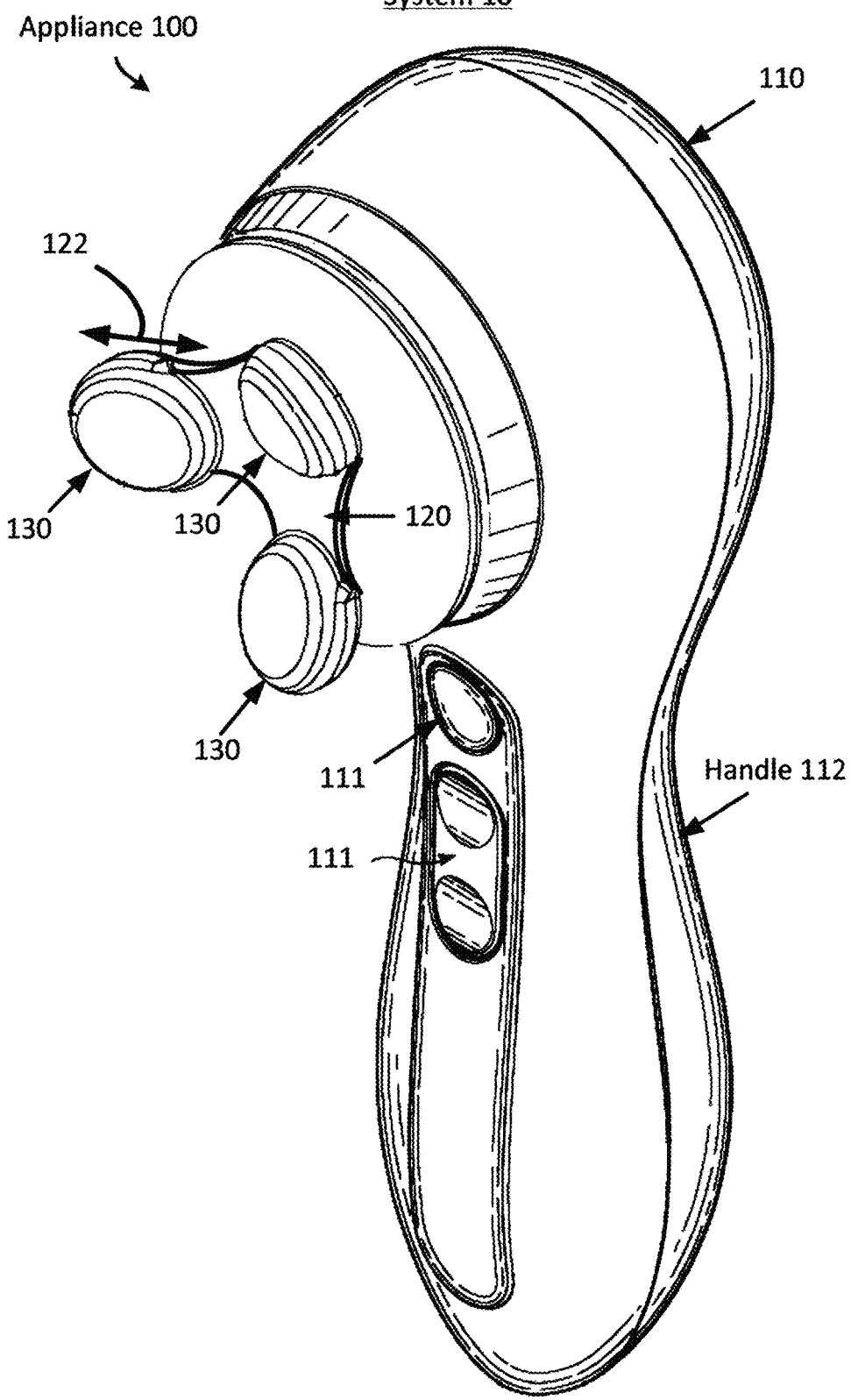

FIG. 1C shows an embodiment the appliance 100 having a handle 112 and the one or more user input mechanisms or buttons 111 on the handle 112.

FIG. 1D shows an embodiment the appliance 100 having a handle 112 and the grip electrode 113 on the handle 112. In this case, the grip electrode 113 is positioned on a handgrip of the handle 112 having an ergonomic shape such that the grip electrode 113 is in contact with the subject's skin when the appliance 100 is held. U.S. Pat. No. 7,069,073 "Electrokinetic delivery of medicaments" incorporated herein by reference in its entirety teaches that the return electrode can be located in the handle.

Figure 1E:
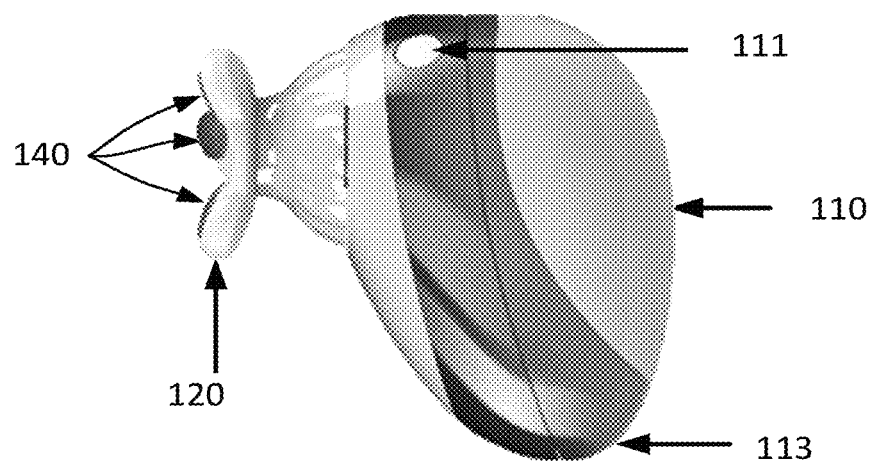

FIG. 1E shows a perspective illustration of a representative system 10 in accordance with the disclosed embodiment in FIG. 1B.

Figure 1F:
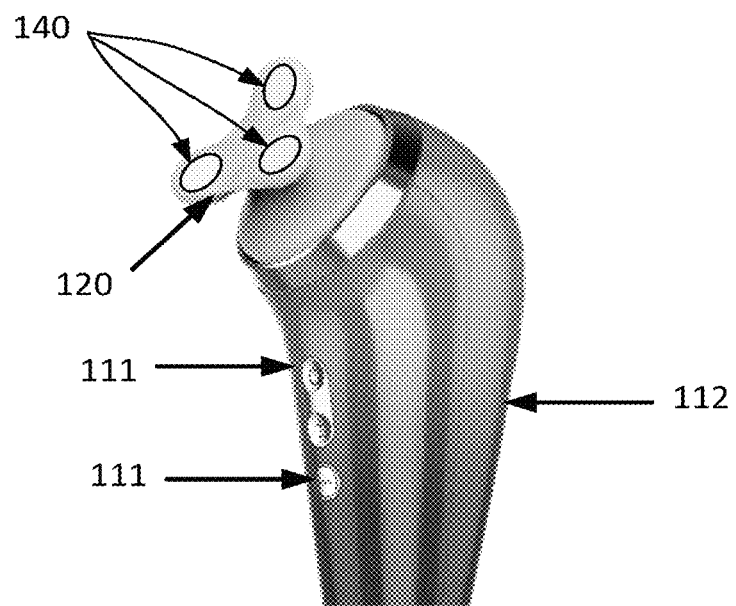

FIG. 1F shows a perspective illustration of a representative system 10 in accordance with the disclosed embodiment in FIG. 1C.

Device Head

According to one embodiment, the device head 110 can have a source of oscillatory or reciprocating mechanical motion and an electrical system 200.

In one aspect, the device head 110 includes a source of oscillatory or reciprocating mechanical motion at a sonic frequency. As used herein, the term "oscillatory" refers to motion that is a regular periodic motion bi-directionally about a neutral position in a plane largely parallel to the skin surface. As used herein, the term "reciprocating" refers to motion that is a regular periodic motion bi-directionally about a neutral position in a plane largely perpendicular to the skin surface. These two terms are not mutually exclusive and both motions can be combined create more complex motions.

Regardless of the type of motion used, the motion is restricted to displacements within the elastic range of skin. That is, the displacements that cause strain remain within the range where elastin is the dominant load bearing protein in the skin matrix. Beyond the elastic range of skin, the skin would plastically and permanently deform or simply tear.

According to one embodiment the source of mechanical motion is a motor. In one example, the end effector 120 is couplable to a motor that is configured to move the end effector 120. In one example, when the end effector 120 is couplable to a motor and the motor is operating, the motor oscillates the end effector 120 with rotational movements about an axis in the Z-direction. In one example the motor is a source of oscillatory or reciprocating mechanical motion at a sonic frequency. In one example, the oscillatory motion can create rotational movements about an axis in the Z-direction using a wobbler.

In one embodiment, the end effector 120 is used to stimulate a portion of skin at a motion frequency. In one embodiment, the end effector 120 is used to induce a cyclical response within a portion of skin at a target motion frequency. In one embodiment, the end effector 120 is used to apply a cyclical mechanical strain to a portion of skin responsive to an applied potential.

In an embodiment, the device head 110 is configured to manage a duty cycle associated with driving the end effector 120. For example, in an embodiment, the device head 110 includes the electrical system 200 having circuitry configured to manage a duty cycle associated with driving an end effector 120.

In one example, the motion frequency is selected based on a condition of the portion of skin. For example, the motion frequency is selected based on an anti-aging effect that is activated by cyclical mechanical strain of the portion of skin at the motion frequency. The embedded electrodes 130 are located at a target distance from each other based on an inverse of the motion frequency. For example, with a motion frequency of 60 Hz, the inverse of the motion frequency (i.e., the period) is 0.0167 seconds per cycle. With a propagation speed of 2.0 meters per second, the wavelength is 0.0333 meters per second, or 3.33 cm per second. Other examples of wavelength distances based on frequency are shown in TABLE 1.

TABLE 1

Example wavelength distances based on frequency

| Frequency (f) Hz (cycle/sec) | Period (T) (sec/cycle) | Speed (v) (m/s) | Wavelength (λ) (m/cycle) | Wavelength (λ) (cm/cycle) |
|---|---|---|---|---|
| 60 | 0.0167 | 2.0 | 0.0333 | 3.33 |
| 65 | 0.0154 | 2.0 | 0.0308 | 3.08 |
| 70 | 0.0143 | 2.0 | 0.0286 | 2.86 |
| 75 | 0.0133 | 2.0 | 0.0267 | 2.67 |
| 80 | 0.0125 | 2.0 | 0.0250 | 2.50 |
| 85 | 0.0118 | 2.0 | 0.0235 | 2.35 |
| 90 | 0.0111 | 2.0 | 0.0222 | 2.22 |
| 95 | 0.0105 | 2.0 | 0.0211 | 2.11 |
| 100 | 0.0100 | 2.0 | 0.0200 | 2.00 |
| 105 | 0.0095 | 2.0 | 0.0190 | 1.90 |
| 110 | 0.0091 | 2.0 | 0.0182 | 1.82 |
| 115 | 0.0087 | 2.0 | 0.0174 | 1.74 |
| 120 | 0.0083 | 2.0 | 0.0167 | 1.67 |

In one embodiment, the embedded electrodes 130 are located at a distance from each other that is a whole integer increment of the inverse of the motion frequency. Using the 60 Hz example above, one whole integer increment of the inverse of the motion frequency is 3.33 cm. Thus, in this 60 Hz example, the distances 341 between the embedded electrodes 130 are 3.33 cm. Using another example with a 110 Hz motion frequency, the wavelength is 1.82 cm per second. One whole integer increment of the inverse of the motion frequency is 3.64 cm. Thus, in this 100 Hz example, the distances 341 between the embedded electrodes 130 are 3.64 cm. Many other examples of frequencies and whole increments of the inverse of the frequencies are possible. In TABLE 1, speed refers to the speed of sound in skin which is approximately 2.0 m/s.

Massage Mode

The mechanical motion is used by the massage mode to deliver a massage or mechanobiology stimuli and aid in relaxation of a subject. The mechanobiology stimuli can be configured to evoke a biomarker generation in the subject. In one embodiment the massage mode performs sonic frequency vibration of the end effector 120. Vibration of the end effector 120 causes each arm 122 of the end effector 120 to vibrate. In one aspect, the vibration of the end effector 120 produces an amplified movement at each arm 122, which can deliver a massage or mechanobiology stimuli and aid in relaxation of a subject.

Oscillatory Mechanical Motion

In one embodiment the source of mechanical motion is a source of oscillating motion that rotates the end effector 120 relative to the device head 110. Rotation of the end effector 120 results in oscillation of the arms 122 parallel to the skin. The source of oscillating motion produces motion at sonic frequencies. In one embodiment, the first source has an oscillation rate of less than 1 kHz. In one embodiment, the first source has an oscillation rate of less than 200 Hz. In one embodiment, the first source has an oscillation rate of greater than 10 Hz. In one embodiment the source of oscillating motion has an oscillation rate of 20 to 1000 Hz. In one embodiment the source of oscillating motion has an oscillation rate of 20 to 80 Hz.

An exemplary device for providing oscillating sonic movement is the Clarisonic Brush (Clarisonic, Redmond, Wash.). U.S. Pat. No. 7,320,691 incorporated herein by reference in its entirety describes an optimal frequency and strain for providing oscillating sonic movement. The oscillating, sonic frequency movement increases the skin's permeability by temporarily flexing and enlarging transappendageal pathways such hair follicles and sweat glands, which in turn increases transdermal flux.

Reciprocating Mechanical Motion

In one embodiment the source of mechanical motion is a source of reciprocating motion. The source of reciprocating motion produces motion at sonic frequencies. In one embodiment, the first source has a reciprocation rate of less than 1 kHz. In one embodiment, the first source has a reciprocation rate of less than 200 Hz. In one embodiment, the first source has a reciprocation rate of greater than 10 Hz. In one embodiment the source of reciprocating motion has a reciprocation rate of 20 to 200 Hz. In one embodiment the source of reciprocating motion has a reciprocation rate of 110 to 135 Hz.

In one embodiment, the source of reciprocating motion is selected from the group comprising of a motor, a pneumatic device, and a piezoelectric device. Such sources of reciprocating motion at sonic frequencies are known to those of skill in the art and can be implemented in the disclosed appliance 100 accordingly.

An exemplary device for providing reciprocating sonic movement is an "Opal" device (Clarisonic, Redmond, Wash.), which is described by U.S. Patent Application Publication No. 2009/0306577, incorporated herein by reference in its entirety. The Opal device has a device head that creates strain on the skin immediately adjacent to the area of the skin that is in contact with the applicator. This action increases skin permeability by temporarily flexing and enlarging dermatoglyphs, paracellular spaces or transappendageal pathways such as hair follicles and sweat glands, which in turn increases dermal delivery. The action of the Opal device head, which is substantially perpendicular to the skin, also acts to drive a formulation into the epidermis. This driving force occurs regardless of the formulation composition.

Figure 2A:
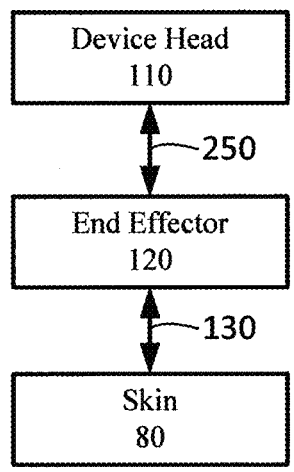
FIGS. 2A-B show a flow diagram depicting high-level embodiments of the electrical circuit loops formed between the system and the skin.
Figure 2B:
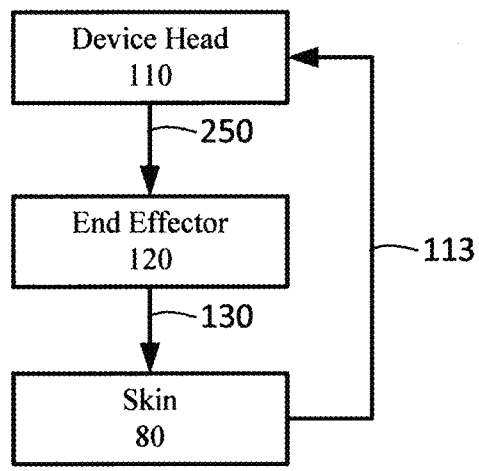

FIGS. 2A-B show a flow diagram depicting high-level embodiments of the electrical circuit loops formed between the system 10 and the skin 80. FIG. 2A shows a first embodiment of the electrical circuit (A) where the device head 110 is connected to the end effector 120 by electrical wiring 250, where in the embedded electrodes 130 on the end effector 120 are in electrical communication with the skin 80 and/or the treatment area 81. The electrical wiring 250 can include wires, metal contacts, circuit board traces and the like.

FIG. 2B shows a second embodiment of the electrical circuit (B) where the device head 110 is connected to the end effector 120 by the electrical wiring 250, where in the embedded electrodes 130 on the end effector 120 are in electrical communication with the skin 80 and/or the treatment area 81, and wherein the electric circuit is completed back to the device head 110 through the grip electrode 113.

Further examples of electrical circuits can be formed for the different modes. For instance, in an example with a plurality embedded electrodes 130 and one grip electrode 113 on the device head 110, current can be driven in one of the following configurations:

a. Into the skin from all embedded electrodes 130 concurrently for global infusion of the actives in the iontophoresis mode;
b. Out of the skin from all embedded electrodes 130 concurrently for global removal of impurities in the iontophoresis mode;
c. In between any pair of embedded electrodes 130 for tightening of the skin in the microcurrent mode.

The operating principle is that microcurrents are applied through multiple embedded electrodes 130 and that those embedded electrodes 130 are not rigid relative to each other. Microcurrents can be applied through pairs of embedded electrodes 130 that are spatially flexible relative to each other. By using different numbers of embedded electrodes 130 and different spatial orientations of the electrode assembly 140, multiple electrical pathways can be created to spread the current with patterns relative to the skin. In an aspect, the microcurrents can be configured to supply power to the electrode assembly 140 resulting in different spatial distributions of current to the treatment area 81. Microcurrents can be configurable to result in switchable polarity of each embedded electrode 130.

Figure 2C:
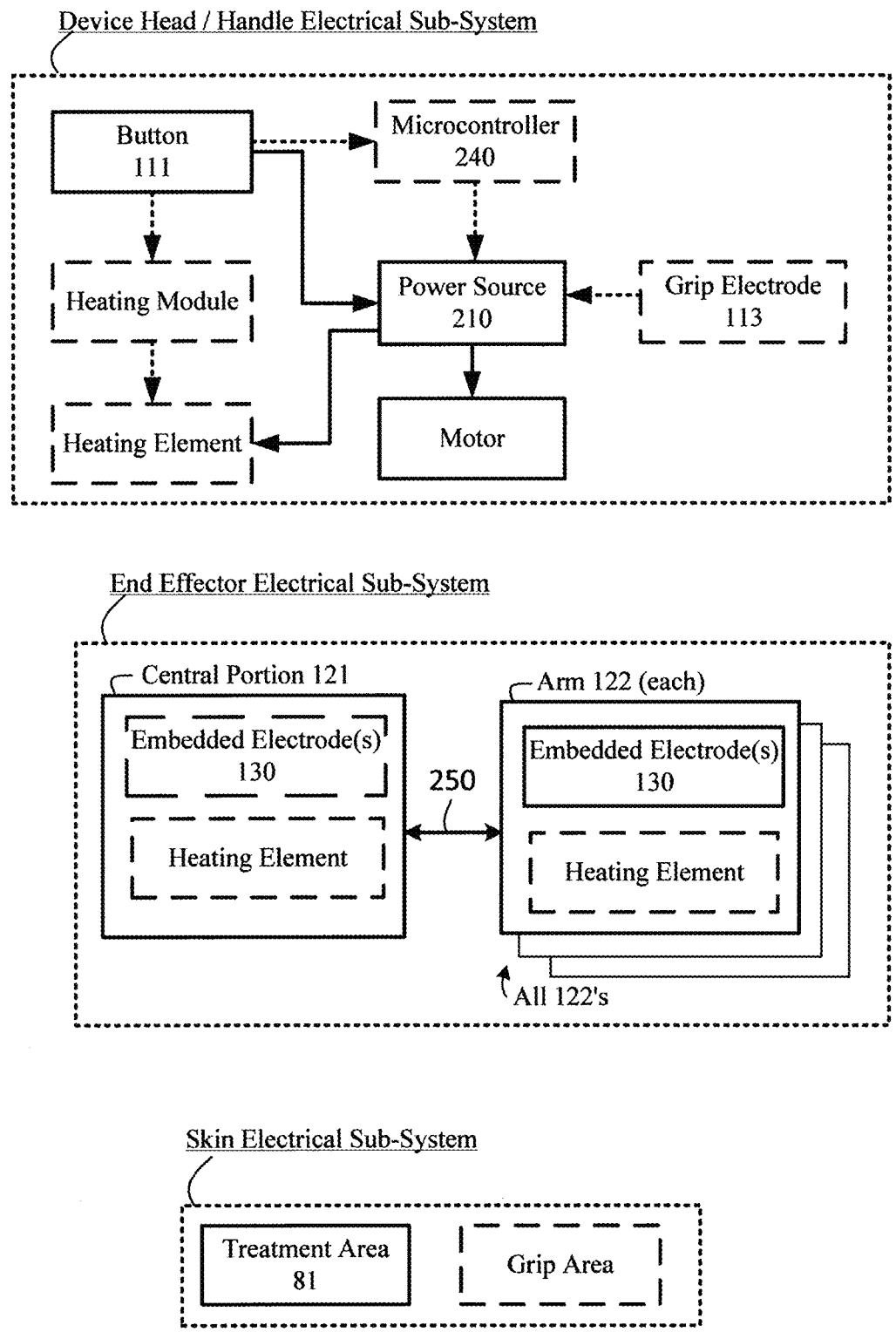
FIG. 2C shows multiple examples of electrical subsystems for different embodiments of the appliance and the portions of the skin.

FIG. 2C shows multiple examples of electrical sub-systems for different embodiments of the appliance 100 and the portions of the skin 80. The electrical sub-system for the device head 110 is shown including a power source 210, a motor, and the button 111. Optionally the electrical sub-system for the device head 110 can include a microcontroller 240, a heating module, a heating element, and the grip electrode 113. In one example, the electrical system 200 can include the power source 210 directly in electrical communication with the heating element or separately controlled by the heating module. The electrical sub-system for the end effector 120 is shown with different examples for the central portion 121 and for each arm 122 on the end effector 120. The central portion 121 is shown with the embedded electrodes 130 and the heating element being optional. Each arm 122 is shown with at least one embedded electrode 130 and the heating element being optional. The electrical sub-system for the skin 80 includes the treatment area 81 and optionally the grip area which is in communication with the grip electrode 113.

Figure 2D:
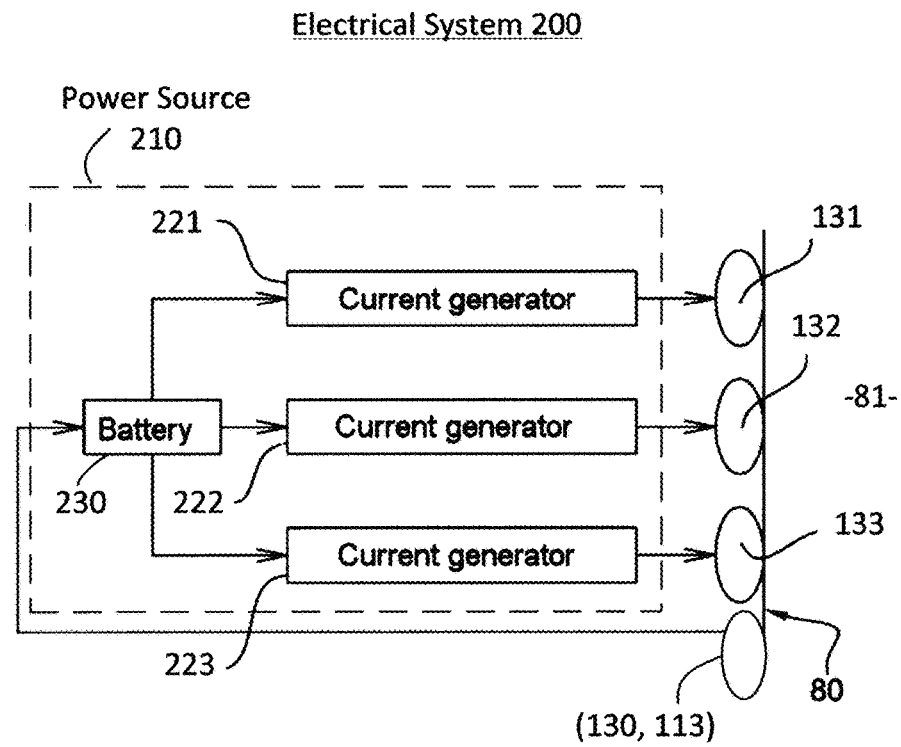
FIG. 2D shows a schematic of the electrical system including a power source in direct electrical communication with the embedded electrodes according to a first embodiment.

FIG. 2D shows a schematic of the electrical system 200 including the power source 210 in direct electrical communication with the embedded electrodes 130 according to a first embodiment. In one example, the power source 210 can have a plurality of current generators 220 that are each connected to a respective embedded electrode 130. In this case, each embedded electrode 130 can be managed by a controlling circuit or its dedicated current generator 220.

In the example shown, the three current generators 221, 222 and 223 each output a current with a given power to three embedded electrodes 131, 132 and 133 respectively. In an aspect, each embedded electrode 131, 132 and 133 is managed by its respective current generator 220 that is configured to deliver a given current intensity in a spatial distribution according to the electrode assembly 140. The current is transmitted to the treatment area 81 by the electrode assembly 140. The embedded electrodes 131, 132 and 133 are electrically insulated and are managed independently of one another so as to adapt the current intensity to a number of embedded electrodes 130 that are in contact with the skin.

Together, when the appliance 100 is in electrical communication with the skin the electrical circuit is formed. When at least one embedded electrode 130 and the grip electrode 113 are in contact with the subject's skin, the electrical circuit connecting the embedded electrode 130 to the skin is closed. In this case, power at the embedded electrode 130 is provided. When at least one embedded electrode 130 and the grip electrode 113 are not in contact with the skin, the electrical circuit connecting this embedded electrode 130 to the skin is open. In this case, power at the open embedded electrode 130 is not provided.

Figure 2E:
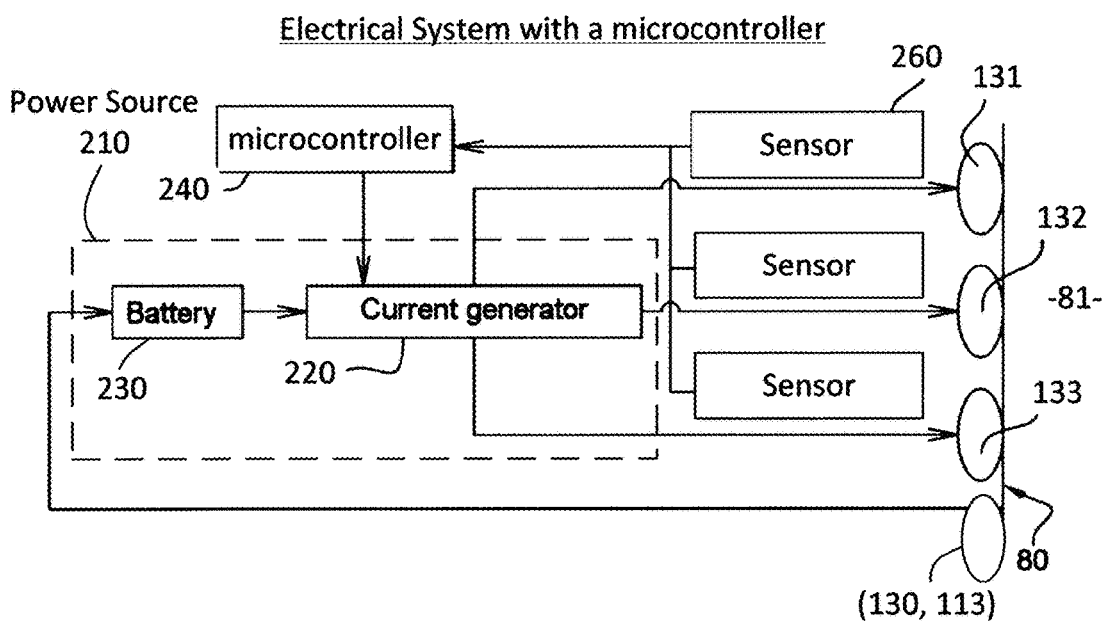
FIG. 2E shows a schematic of an electrical system including the power source in electrical communication with a microcontroller, the embedded electrodes according to a second embodiment.

FIG. 2E shows a schematic of the electrical system 200 including the power source 210 in electrical communication with a microcontroller 240, the embedded electrodes 131, 132 and 133 and a series of sensors 260 according to a second embodiment. In this embodiment the power source 210 can include the battery 230 and only one current generator 220 or less current generators than the number of the embedded electrodes 130, where the microcontroller 240 is configured to control the power to each embedded electrode 130. According to an example, the microcontroller 240 can further include a microprocessor.

In the example shown, the three embedded electrodes 131, 132 and 133 can be connected in parallel to the current generator 220. In one case, the three embedded electrodes 131, 132 and 133 connected in parallel to the current generator 220 and in electrical communication with the skin can form a single electric circuit. In another case, the three embedded electrodes 131, 132 and 133 connected in parallel to the current generator 220 and in electrical communication with the skin can effectively form multiple electric circuits. In parallel operation, each embedded electrode 130 in electrical communication with the skin represents a loop in the electric circuit. Within each loop in the electrical circuit, the sensor 260 can be configured to detect a presence of current flow, which is communicated to the microcontroller 240.

The microcontroller 240 and the sensor 260 can be configured to monitor effectiveness of the treatment and homogeneity of the current in the treatment area 81, in particular at the skin periphery. To this end, the microcontroller 240 can be configured to control a voltage between each embedded electrode 130 and the grip electrode 113 in order to regulate the current generated by the current generator 220.

The power source 210 and/or the microcontroller 240 can be configured to output power in according to several scenarios. The power can be configured to form the same or different voltage and current profiles to each embedded electrode 130. In one embodiment, the power can be configured to modify the current density of each embedded electrode 130 such that there is a maintained or unique spatial current density applied to the treatment area 81 according to the electrode assembly 140 or the function mode.

Figure 2F:
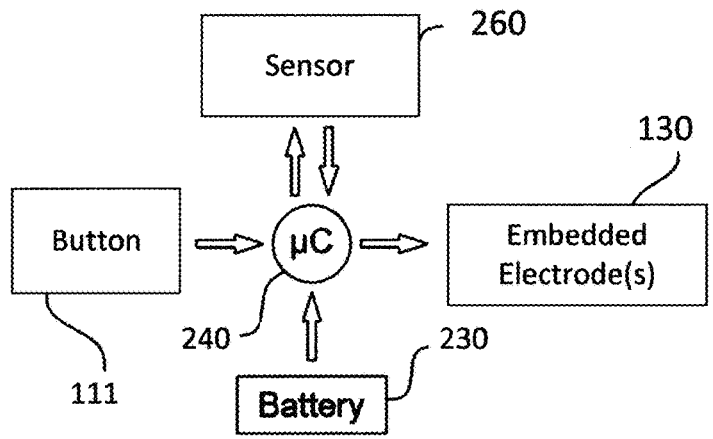
FIG. 2F is a flowchart showing detail of electrical communication to the microcontroller according to a second embodiment of the invention.

FIG. 2F is a flowchart showing detail of the electrical communication to the microcontroller 240 according to the second embodiment of the invention. In this example the appliance 100 includes the embedded electrodes 130, and the electrical system 200 having the battery 230, the sensor 260, the microcontroller 240, and the button 111. The microcontroller 240 is configured to control the current intensity at the embedded electrodes 130 depending on the input provided by the sensor 260 and on the button 111 indicating the type of care desired.

The microcontroller 240 is supplied with power by the battery 230 and receives the data measured by the sensor 260. The microcontroller 240 also receives on/off commands and programming from the button 111 actuated by the subject. The button 111 may be mechanical or tactile. The microcontroller 240 can also be configured to cause the display of information on a screen or an indicator so that the subject can see the operating mode of the appliance 100.

In another embodiment, the appliance 100 can further include an accelerometer and/or a gyroscope can be configured to detect an orientation of the appliance 100 relative to the subject. The accelerometer and/or the gyroscope can communicate their output to the microcontroller 240, which can modify the stimulation waveform can change based on the accelerometer and gyroscope & maintain field pattern with underlying tissue fibers.

Figure 2G:
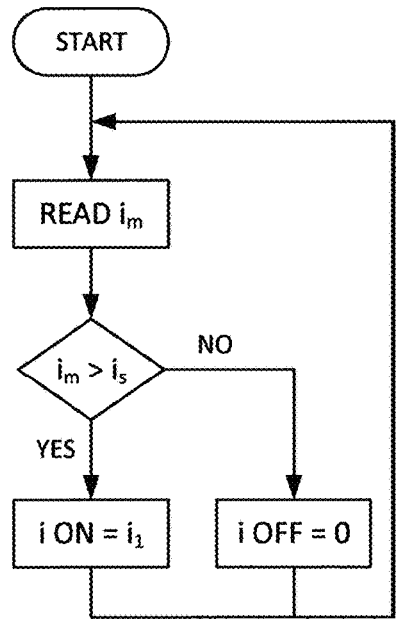
FIG. 2G shows a flowchart of a program implemented by the microcontroller according to the second embodiment of the invention.

FIG. 2G shows a flow chart of a program implemented by the microcontroller 240 according to the second embodiment of the invention. When the appliance 100 is activated (START) and a program is chosen by the subject, the microcontroller 240 collects an item of read data for a current measured ($i_m$) from the sensor 260. The current measured ($i_m$) is compared with a threshold current value ($i_s$) by the microprocessor.

In the example shown, the current values for each embedded electrode 130 are fixed as follows: $i_s = -10$ µA, a predetermined current value ($I_1$) is identified in order to reach a current intensity per unit area that is equal to 0.3 mA/cm². If ($i_m$)>($i_s$), then the current generator 220 delivers a current from the power source 210 at the embedded electrode 130 that ranges up to the predetermined current value ($I_1$). (i ON=$I_1$) is then the case at the embedded electrode 130. If ($i_m$)<($i_s$), then the current generator 220 does not deliver any additional current at the embedded electrode 130. A standby situation is then the case. (i OFF) is then the case at the embedded electrode 130.

The appliance 100 may include an indicator light and/or a loudspeaker for informing the subject in a sensory manner that the output of current from at least one embedded electrode 130 has been interrupted because the appliance 100 is being held too far away from the treatment area 81 in a given location.

More specifically, the output power of each embedded electrode 130 may obey a specific regulating law that depends on the location of the embedded electrode 130 in the appliance 100 (central or peripheral position) and/or that depends on the type of electrode and/or that depends on the current (continuous or pulsed).

Figure 2H:
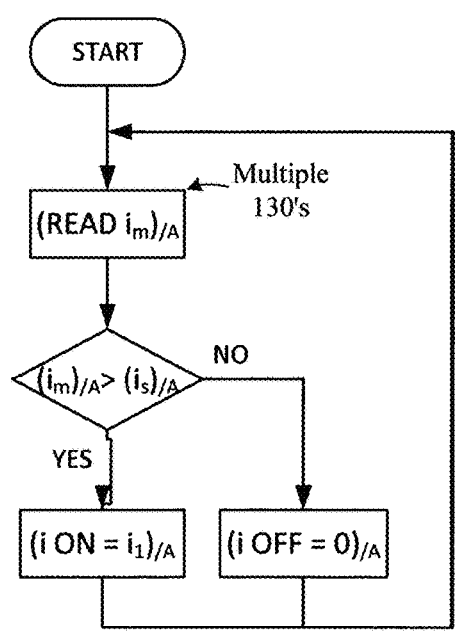
FIG. 2H shows another example of a flowchart of a program implemented by the microcontroller according to the second embodiment of the invention.

FIG. 2H shows another example of a flow chart of a program implemented by the microcontroller 240 according to the second embodiment of the invention. Here the microcontroller 240 collects an item of read data for a current measured ($i_m$) from the sensor 260 for a pair or more embedded electrodes 130, collectively ($i_m$)$_{/A}$. The collective currents measured ($i_m$)$_{/A}$ for the pair or more embedded electrodes 130 are compared with a threshold current value per area ($i_s$)$_{/A}$ by the microprocessor. Here the threshold current value per area can take into account the electrode assembly 140.

End Effector

A first embodiment of an end effector 120 is depicted in FIGS. 3A to 3D using a coordinate system with X-, Y-, and Z-directions. In this embodiment the end effector 120 includes three arms 122 and an embedded electrode 130 on each arm 122.

Figure 3A:
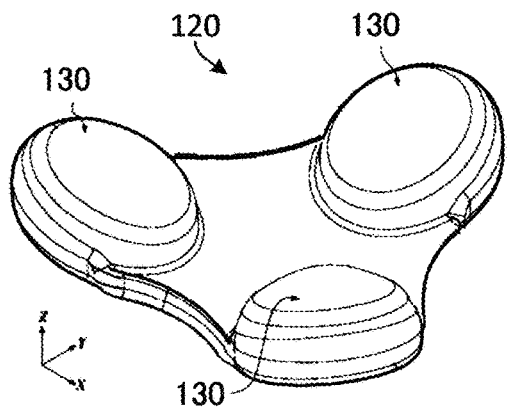
FIGS. 3A to 3D show schematic illustrations of different views of the end effector having a central portion, three arms and an embedded electrode on each arm according to an embodiment.

FIG. 3A shows a schematic view of the end effector 120 according to an embodiment. The end effector 120 is configured to conform to a curvature or contour of the skin surface. In an aspect, the end effector 120 flexes to fit the curves of the human face and maintain proper electrode contact such that the embedded electrodes 130 operably connected to the electrical system 200.

Figure 3B:
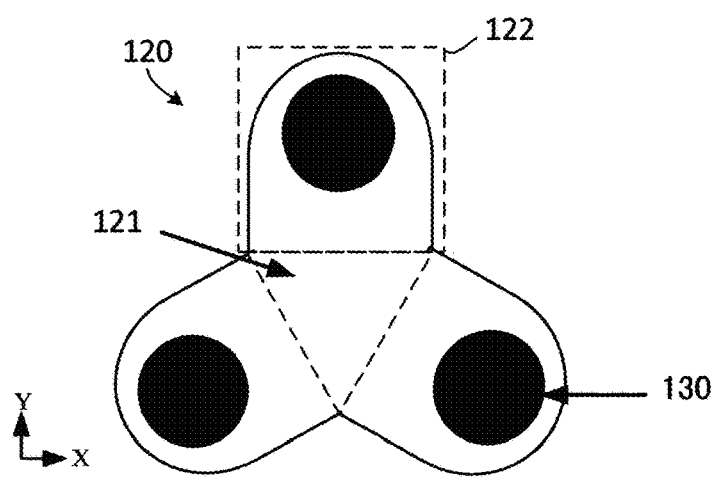

FIG. 3B shows a schematic view of the end effector 120 in the Z-direction according to an embodiment. The end effector 120 is shown includes a central portion 121 located between the arms 122. In the Z-direction, the central portion 121 is depressed from the arms 122 such that the embedded electrodes 130 of the arms 122 are the points at which the arms 122 would contact a flat object lowered in the Z-direction.

In one aspect, the end effector 120 can be made of a generally flexible or compliant material. In one embodiment, the end effector 120 is made of a non-rigid material. Some examples of non-rigid materials include plastics (e.g., polyurethane), elastomeric materials (e.g., thermoplastic elastomers), rubber materials, and any combinations thereof. In one example, the non-rigid material of the end effector 120 has a hardness in a range from about 10 Shore A to about 60 Shore A, as defined by the American Society for Testing and Materials (ASTM) standard D2240.

In another aspect, each arm 122 of the end effector 120 can have a distal end, a proximal end, and a main portion. The proximal end of each arm 122 is connected to the central portion 121. In this case, only the main portion of each arm 122 can be made of a flexible or compliant material. Alternatively, the proximal end of each arm 122 can be connected to the central portion 121 of the end effector 120 by a hinged spring connector, or an alternate mechanical system to provide for the arms 122 of the end effector 120 to conform to the curvature of the skin surface. In this case, the arms 122 of the end effector 120 can be made of a stiffer material.

In one embodiment, the end effector 120 may have a plurality of bristles (not shown). The bristles can be used to enhance the mechanobiology stimuli of the massage mode or to mask the sensations of either the iontophoresis mode or the microcurrent mode. In one example, the bristles can surround each embedded electrode 130 individually and can be separated from bristles of the other embedded electrodes 130. In this case the bristles can be used for their enhancements without creating shunt pathways for electrical current between two or more embedded electrodes 130.

Figure 3C:
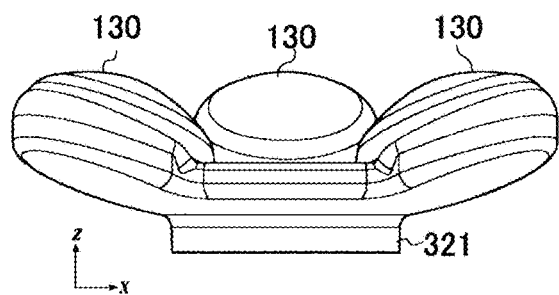

FIG. 3C shows a perspective illustration of a representative end effector in the Y-direction in accordance with the disclosed embodiment in FIG. 3A. The end effector 120 is shown including a central support 321 on the opposite side of the central portion 121. As is seen in FIG. 3C, the arms 122 are located on portions of end effector 120 that are cantilevered out from the central support 321. When the end effector 120 is made of a non-rigid material and the arms 122 are located on portions of end effector 120 that are cantilevered out from the central support 321, the portions of end effector 120 with the arms 122 have a spring-like quality that permits some movement of the arms 122 in the Z-direction.

Figure 3D:
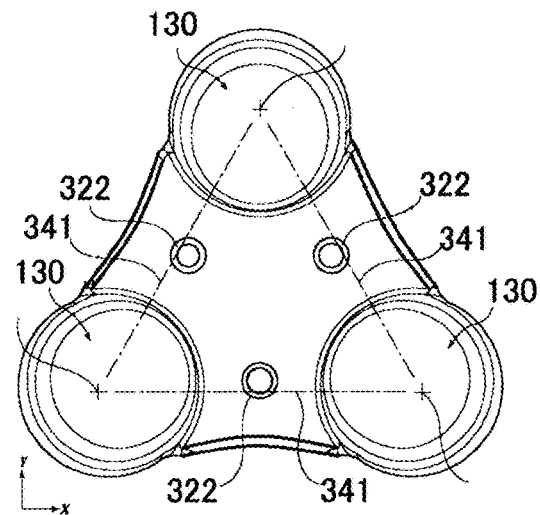

FIG. 3D shows another schematic view of the end effector 120 in the Z-direction according to an embodiment. In an aspect, the embedded electrodes 130 are located a target distance 341 away from each other. For example, in an embodiment, the embedded electrodes 130 are located a target distance 341 away from each other determined from the inverse of the motion frequency. In the particular embodiment shown in FIGS. 3A to 3D, the embedded electrodes 130 include the embedded electrodes that are equidistant from each other (i.e., the distances 341 between embedded electrodes 130 are all about the same, such as being within ±5% of each other). In the embodiment shown in FIG. 3D, the end effector 120 includes fastener holes 322. In one embodiment, mechanical fasteners (e.g., screws, bolts, rivets, etc.) are placed in the fastener holes 322 to mechanically fasten the end effector 120 to another component.

Figure 3E:
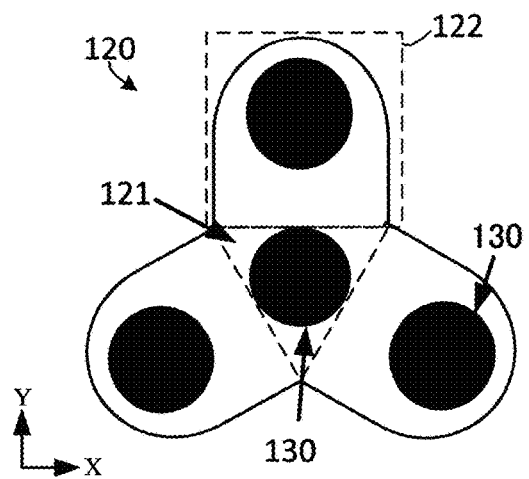
FIG. 3E shows a schematic illustration of top perspective of a representative end effector in accordance with another example of the disclosed embodiments.

FIG. 3E shows a schematic illustration of top perspective of a representative end effector 120 in accordance with another embodiment including a set of contact points 323. In this example, the central portion 121 includes one or more additional embedded electrodes 130, at least one of which can function as the return/counter/ground electrode to complete the electric circuit.

Figure 3F:
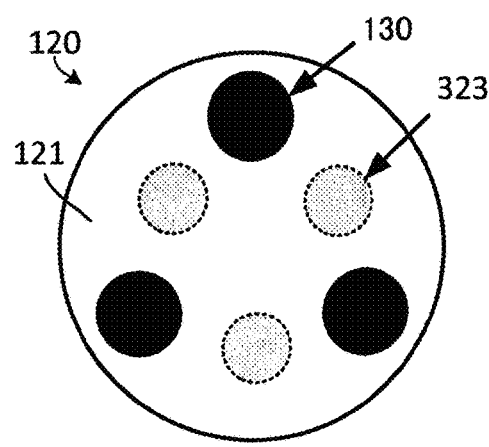
FIG. 3F shows a schematic illustration of top perspective of a representative end effector including a set of contact points in accordance with another embodiment.

FIG. 3F depicts a top view of another embodiment of the end effector 120 having a central portion 121 with different numbers and arrangements of the embedded electrodes 130. In this embodiment, the arms 120 are not required and the end effector 120 can have a uniform outer shape.

The set of contact points 323 are shown on the end effector 120, which can be included in any of the other embodiments in the central portion 121 and/or the arms 120. In one embodiment, each contact point 323 can be used for the providing the mechanical stimuli. In another embodiment, one or more of the contact points 323 can have a sensor 260 configured for measuring or detecting current flow. In another embodiment, one or more of the contact points 323 can have a heating element configured to providing heat to the skin 80.

Figure 3G:
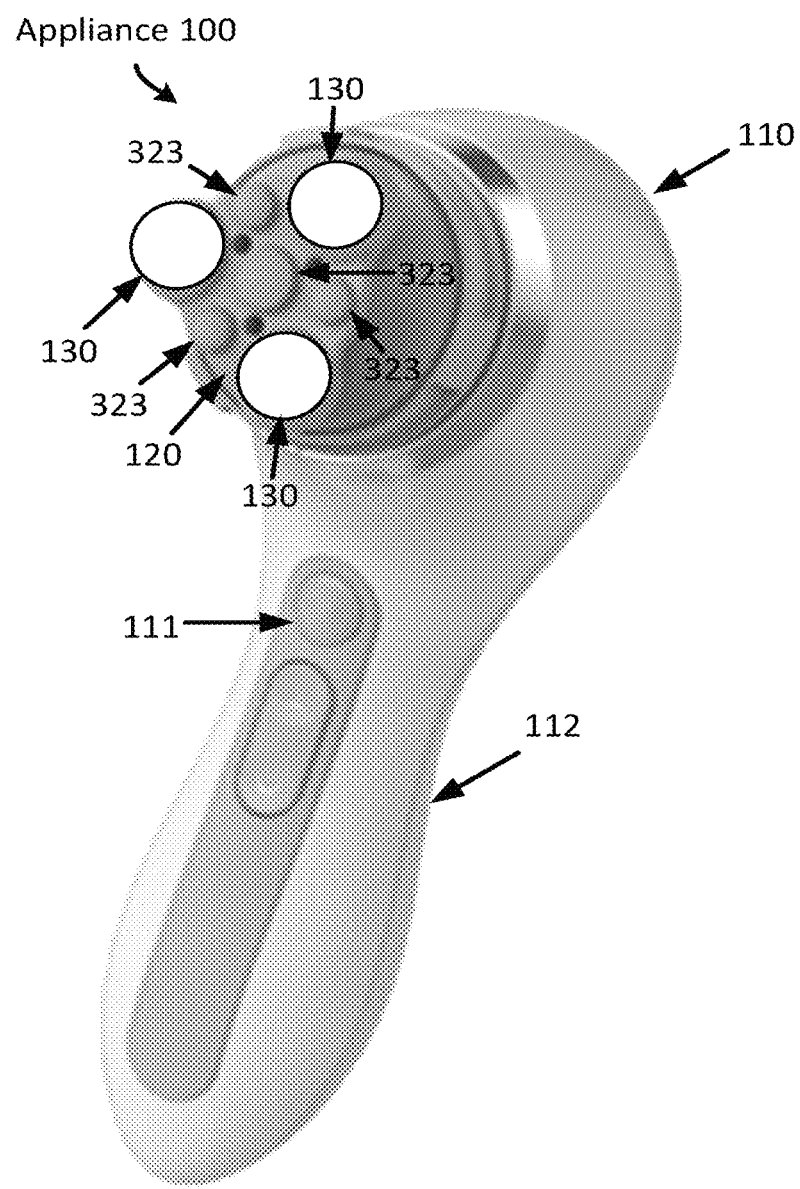
FIG. 3G shows an example of the appliance further including the set of contact points in accordance with another embodiment.

FIG. 3G shows an embodiment the appliance 100, similar to that in FIG. 1C, further including the set of contact points 323.

Embedded Electrode

In an aspect, the end effector 120 can have a plurality of embedded electrodes 130 forming the electrode assembly 140 disposed on the device head 110 with each embedded electrode 130 configured to be in electrical communication with the subject's skin and the power source 210.

In an embodiment, each embedded electrode 130 can take a variety of shapes, configurations, and geometries including spheroidal, polygonal, cylindrical, conical, planar, parabolic, as well as regular or irregular forms.

Each embedded electrode 130 can operate as a source electrode or as a return electrode. Design considerations for the source electrodes include maximizing surface area and conductivity, frictional characteristics, mass and inertial characteristics, and material compatibility and safety. Design considerations for the return electrodes include maximizing surface area and conductivity as well as material compatibility and safety. The return electrode is separate from the location on the subject's skin where the source electrode contacts. As disclosed above, the return electrode may be the grip electrode 113 that is integrated into the device head 110 or the handle 112. In one example any of the embedded electrodes 130 on the end effector 120 can be configured to act as a return electrode that is in electrical communication with a separate location of the subject's skin simultaneously during operation from that of the remaining embedded electrodes 130.

In one embodiment any one of the plurality of embedded electrodes 130 on the end effector 120 can alternate between functioning as a source electrode, a return electrode, and the grip electrode 113.

Each embedded electrode 130 can be controlled individually such that when one embedded electrode 130 gets disconnected, the other embedded electrodes 130 remain functioning. The appliance 100 according to the invention makes it possible to detect the embedded electrodes 130 in contact with the skin and to selectively supply only these embedded electrodes 130 with power.

Iontophoresis Mode

The iontophoresis mode can enable infusion of ionic actives in presence of an applied electrical field. Each of the embedded electrodes 130 can infuse actives. In another example, the iontophoresis mode can enable removal of impurities in presence of an applied electrical field.

Electrical current is applied to the subject's skin via a first embedded electrode 131 on the device head 110 and a second electrode (e.g. 132, 113) in a separate location on the subject's skin. By placing the two electrodes apart on the skin, an electric field gradient is generated that can drive charged actives into the skin (e.g. via iontophoresis). Synergistic effects can be achieved by using iontophoresis to drive the active into the skin at the location which is being impacted by the mechanical force of the device head 110 increasing skin permeability.

Electrical Characteristics

Previous research has shown that the maximum iontophoretic current used for humans should not exceed 0.5 mA/cm$^2$. Voltages between 10 V-30 V have been shown to result in reduced resistance in the skin.

Electrical characteristics for the disclosed devices include constant DC current in one embodiment. In another embodiment an AC signal can be used (e.g., pulsed waveform of 1 kHz with a 60% duty cycle).

In one embodiment the electrical system 200 is configured to maintain a constant current density when used on the subject, wherein the constant current density is maintained by periodic adjustment to an applied voltage. In one embodiment the electrical system 200 is configured to provide a current density of up to 0.5 mA/cm$^2$.

As disclosed in the Examples below, an unexpected effect of the combination of mechanical motion and iontophoresis is that the mechanical motion serves to "mask" the sensation from the applied electrical current used for iontophoresis.

Because of this masking the amount of current that can be applied before a subject perceives the electrical current (reaching the perception threshold current, thus producing discomfort) is increased. This increase in current serves to further drive the iontophoresis and better dermal delivery of the active can be achieved. In the experimental results presented below an average increase of subject perception threshold current was greater than 100% when comparing the non-stimulated perception threshold to the mechanically stimulated perception threshold current. Accordingly, in one embodiment the electrical current used on a subject is increased by 100% or more compared to the subject's non-stimulated perception threshold current.

Increased Perception Threshold

Mechanical stimulation can override nervous response to electrical stimulation from iontophoresis, allowing for increased comfort at higher doses. An initial experiment was conducted to explore and quantify the effectiveness of combining oscillating mechanical shear strain of the skin with iontophoresis for increasing the minimum current delivered to for it to be perceived by a subject. Six (n=6) subjects of varying age and gender used a device with only one embedded electrode 130 coupled with a smooth, chrome plated return electrode to deliver an electric current via an aqueous gel to the forearm, first with the massage mode OFF and then with the massage mode ON where the embedded electrode 130 was oscillating at 170 Hz. Current was controlled using a current limited DC power supply with a maximum output voltage of 30 V. Because the current delivered is a function of the applied voltage and the electrical resistance of the subject, a high enough current was not able to be generated to pass the perception threshold in certain subjects. In the event that the maximum output voltage was reached before crossing a subject's perception threshold, the final current in mA was recorded. In the event that the current output went above the 0.5 mA/cm$^2$ recommended limit, the experiment was terminated.

TABLE 2 shows the results of the perception threshold experiment. Ignoring results where a conclusive threshold could not be achieved, there was still an average of a 150% increase in current delivered before crossing a subject's perception threshold. While illustrative embodiments have been illustrated and described, it will be appreciated that various changes can be made therein without departing from the spirit and scope of the invention.

TABLE 2

Increased Perception Threshold

| Subject | Perception Threshold (mA) | | Percent Increase | Note |
|---|---|---|---|---|
| | Oscillation Off | Oscillation On | | |
| 1 | 1.6 | 3.6 | 125% | max voltage reached |
| 2 | 0.2 | 0.58 | 190% | |
| 3 | 1.2 | 2.5 | 108% | |
| 4 | 0.6 | 1.5 | 150% | |
| 5 | 1.6 | 5 | 213% | experiment stopped |
| 6 | 3 | 3.5 | 17% | max voltage reached |

Formulation

In various embodiments, the formulations described herein are one or more of a cosmetic composition (e.g., makeup, foundation, bronzer, etc.), a medical ointment (e.g., antibacterial ointment, hydrocortisone cream, etc.), a cleanser (e.g., soap, makeup remover, etc.), or any other composition that is capable of being applied to a portion of skin. In various embodiments, the formulation is a liquid, a non-Newtonian substance, a gel, or any other type of composition. The formulation can be configured for uses such as skin care, skin cleansing, skin purification, skin exfoliation, skin desquamation, massage, cellulite, thinning, make up, and depigmentation.

Integral to the effective function of the appliance 100 is an appropriately formulated topical solution that contains the ionic form of active ingredients desired. The formulation is positioned between the subject's skin and each embedded electrode. In one embodiment, the formulation is applied to the device head 110 prior to contacting the subject's skin. In one embodiment, the formulation is applied to the location on the subject's skin prior to the steps of directing the sonic motion and directing the ultrasonic motion. In one embodiment, the formulation improves action between the location and the first source of oscillatory motion. In one embodiment, the formulation improves action between the location and the second source of oscillatory motion. In one embodiment the appliance 100 includes a formulation reservoir configured to deliver the formulation between the subject's skin and the first electrode.

In one embodiment, the formulation can have a pH and ion concentration (both active and competing) to maximize the flux of the active into the epidermis.

In one embodiment the formulation includes a charged species of an active ingredient selected from the group comprising of analgesics, anesthetics, anti-inflammatories, anticoagulants, therapeutic peptides, oligonucleotides, and cosmetic actives.

In one embodiment the formulation includes an active ingredient selected from the group comprising of aspirin, atropine, caffeine, epinephrine, hyaluronic acid, insulin, L-ascorbic acid and derivatives thereof, lidocaine, hbFGF, ribonuclease, and RNAse T1.

In one embodiment the formulation includes an active ingredient selected from humectants and moisturizing ingredients, and anti-aging actives. Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestlé under the name NutraLipids, a C-glycoside derivative such as those described in WO 02/051828 and in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestlé, a micro-algae extract *Prophyridium cruentum* enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

In one embodiment the formulation includes a depigmenting agent. Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Preferred depigmenting agents include vitamin C and its derivatives and especially vitamin CG, CP and 3-O ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

In one embodiment the formulation includes an anti-wrinkle active. As used herein, the term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines.

Exemplary anti-wrinkle actives may be chosen from: desquamating agents, anti-glycation agents, inhibitors of NO-synthase, agents mechanically stimulating the synthesis of dermal or epidermal macromolecules and/or preventing their degradation, agents for mechanically stimulating the proliferation of fibroblasts and/or keratinocytes, or for mechanically stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinyl palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-} acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists including adenosine adenosine phenylisopropyl ("PIA"), 1-méthylisoguanosine, N6-cyclohexyladenosine (CHA), N6-cyclopentyladenosine (CPA), 2-chloro-N6-cyclopentyladenosine, 2-chloroadenosine, N6-phényladénosine, 2-phénylaminoadénosine, MECA, N 6-phénéthyladénosine, 2-p-(2-carboxy-ethyl)_phenethylamino-5'-N-ethylcarboxamido adenosine (CGS-21680), N-ethylcarboxamido-adenosine (NECA), the 5'(N-cyclopropyl)-carboxamidoadénosine, DPMA (PD 129.944) and metrifudil.

Other adenosine derivatives include compounds that increase the intracellular concentration of adenosine, such as erythro-9-(2-hydroxy-3-nonyl) adenine ("EHNA") and iodotubercidine. Others adenosine derivatives include salts and alkyl esters.

By C-glycoside derivative, is meant in particular the compounds described in EP-1345919 of the formula (I): R-SIX (A) wherein S represents a monosaccharide or a polysaccharide up to 20 units sugar in pyranose and/or furanose form and of L and/or D, said mono- or polysaccharide having at least one hydroxyl function that is necessarily free and/or optionally one or more optionally protected amine functions, the bond S—CH 2-X represents a bond of C-anomeric nature, X represents a group selected from: —CO—, —CH(OH)—, —CH (NR1 R2)-, —CHR'—, —C (═CHR')—, R represents a linear or branched alkyl, perfluoroalkyl chain, hydrofluoroalkyl, saturated or unsaturated cycloalkyl ring, cycloperfluoroalkyl cyclohydrofluoroalkyl comprising from 1 to 18 carbon atoms, phenyl or benzyl, said channel, said ring or said radical can be optionally interrupted by one or more heteroatoms selected from oxygen, sulfur, nitrogen, silicon, and optionally substituted with at least one radical chosen from —Or'l, —SR's, —NR"R'2'1, —COOR"2, —CONHR" '2, —CN, halogen, perfluoroalkyl, hydrofluoroalkyl and/or at least one cycloalkyl radical, aryl, optionally substituted heterocyclic, R', R1, R2, identical or different, have the same meaning as that given for R, and can also be hydrogen and a hydroxyl radical, R'1, R'2, R"1, R" 2, R'''1, R'''2, identical or different, represent a hydrogen atom, hydrogen, a radical selected from alkyl, hydroxy, perfluoroalkyl and/or hydrofluoroalkyl, linear or branched, saturated or unsaturated, comprising from 1 to 30 carbon atoms.

An active promoting skin microcirculation assets acting on the cutaneous microcirculation can be used to avoid dulling of the complexion and/or improve the appearance of the eye contour, in particular to reduce dark circles. The active may for example be selected from an extract of maritime pine bark as Pycnogenol (R) from Biolandes, manganese gluconate (GIVOBIO GMn Seppic), an extract of Ammi Visnaga as Visnadine of Indena, lupine extract (Eclaline Silab), the coupling protein hydrolyzed wheat/palmitic acid with palmitic acid as Epaline 100 Carilene Laboratories, the extract of bitter orange blossom (Remoduline Silab) vitamin P and its derivatives such as methyl-4 monoéthanoate esculetol sodium sold under the name Permethol Sephytal, extracts of ruscus, brown guinea, ivy, sweet clover and ginseng, caffeine nicotinate and derivatives thereof, lysine and its derivatives such as Asparlyne Solabia, a black tea extract as Kombuchka Sederma; rutin salts: an extract of the alga *Corallina officinalis*, such as marketed by Codif, and mixtures thereof.

Preferred agents for promoting the cutaneous microcirculation, we include caffeine, extract of bitter orange blossom, a black tea extract, rutin salts, an extract of the alga *Corallina officinalis*.

In one embodiment the formulation includes an active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate; —derivatives particularly copper and copper pidolate as Cuivridone Solabia—extracts from plants of *Arnica montana, Cinchona succirubra, Eugenia caryophyllata, Humulus lupulus, Hypericum perforatum*, Mentha pipenta 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab— extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech; —extracts of *Pygeum afrianum* such as that sold under the name *Pygeum afrianum* sterolic lipid extract by Euromed— extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Sérobiologiques; 25—lactic protein filtrates, such as that sold under the name Normaseb by Sederma— the seaweed *laminaria* extracts, such as that sold under the name Laminarghane by Biotechmarine—oligosaccharides seaweed *Laminaria digitata*, such as that sold under the name Phycosaccharide 30 AC by the company Codif— extracts of sugar cane such as that sold under the name Policosanol by the company Sabinsa, the sulfonated shale oil, such as that sold under the name Ichtyol Pale by Ichthyol—extracts of 'meadowsweet (*Spiraea ulmaria*) such as that sold under the name Cytobiol Ulmaire by sociétéLibiol—sebacic acid, especially sold in the form of a sodium polyacrylate gel under the name Sebosoft by Sederma—glucomannan extracted from konjac tuber and modified with alkylsulfonate chains such as that sold under the name Biopol Beta by Arch Chemical—extracts of *Sophora angustifolia*, such as those sold under the name Sophora powder or *Sophora* extract by Bioland—extracts of *cinchona* bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL (R) ECI by Sasol; trialkyl citrate (C14-C15) sold under the name COSMACOL (R) ECL by Sasol—10-hydroxydecanoic acid, including mixtures acid-hydroxydecanoic October 25, sebacic acid and 1,10-decandiol such as that sold under the name Acnacidol BG by Vincience and—mixtures thereof.

Antiseborrheic active ingredients include: benzoyl peroxide, vitamin B6 (or pyridoxine), 30—zinc salts such as zinc gluconate, zinc pyrrolidonecarboxylate (or zinc pidolate), the zinc lactate, zinc aspartate, zinc carboxylate, zinc salicylate, zinc cysteate—extracts of meadowsweet (*Spiraea ulmaria*), such as that sold under the name Sebonormine (R) by the company Silab—extracts of the alga *Laminaria saccharina*, such as that sold under the name Phlorogine by Biotechmarine—mixtures of extracts of salad burnet root (*Sanguisorba officinalis/Poterium officinale*), rhizomes of ginger (*Zingiber officinalis*) and cinnamon bark (*Cinnamomum cassia*), such as that sold under the name Sebustop by Solabia—extract clove such as that sold under the name Clove extract powder by Maruzen—filtrates lactic such as that sold under the name Normaseb by Sederma protein— extracts of meadowsweet (*Spiraea ulmaria*) such as that sold under the name Cytobiol Ulmaire by Libiol; —sebacic acid, sold especially in the form of a sodium polyacrylate gel under the name Sebosoft by Sederma—glycine grafted onto an undecylenic chain, such as that sold under the name Lipacide UG OR by Seppic—the detrialkyle citrate (C12-C13) sold under the name COSMACOL ECI by Sasol; trialkyl citrate (C14-C15) sold under the name COSMACOL ECL by Sasol—the 10-hydroxydecanoic acid, and especially mixtures of 10-hydroxydecanoic acid, of sebacic acid and of 1,10-decanediol, such as that sold under the name Acnacidol BG by Vincience—and mixtures thereof.

Preferably, the anti-seborrhoeic active agent is chosen from: zinc salts such as zinc gluconate, zinc pyrrolidonecarboxylate (or zinc pidolate), zinc lactate, zinc aspartate, carboxylate zinc, zinc salicylate, zinc cysteate, and preferably pyrrolidonecarboxylate zinc (or Pidolate zinc) or zinc salicylate—the clove extract such as that sold under the name Clove extract powder by Maruzen—glycine grafted onto an undecylenic chain, such as that sold under the name Lipacide UG OR by SEPPIC—trialkyl citrate (C12-C13) sold under the name COSMACOL ECI by Sasol trialkyl citrate (C14-C15) sold under the name COSMACOL 5 ECL by Sasol—and mixtures thereof.

Antiseborrhoeic active is, for example, present in an amount ranging from 0.1 to 10% by weight, preferably 0.1 to 5% by weight, and preferably from 0.5% to 3% by weight, relative to the total weight of the formulation.

Iontophoresis Electrode Materials Selection

The methods, materials, and systems surrounding iontophoresis are described in an extensive literature with much of the physical/chemical analysis and development reported in the 1980's and 90's. Since that period these methods have been refined and perfected such that detailed iontophoresis prescriptions can be made for the infusion of a wide variety of molecules ranging from small molecule metabolites to large proteins on the scale of cytochrome C. This plethora of knowledge can be used to identify the optimal conditions for electrode materials and voltage/current profiles for any given molecular weight, buffer composition, and ionization state. The composition of the electrodes used in iontophoresis can have a substantial effect on the net outcome of percutaneous infusion for a given delivery load. In order to address this subject a product solution is proposed that accounts for the wide variability in formulations and electrodes.

Inert Electrodes

In any electrochemical system where any two metal electrodes are biased as anode and cathode when in contact to a common electrolyte; oxidation and reduction will most likely occur. Generally speaking, for metals immersed in aqueous electrolyte whose electrode potentials are below the absolute value of ±1.23 V, (relative to the standard hydrogen electrode), the anode will oxidize and the cathode will reduce. For those materials that are more inert (having electrode potentials above this value) it is the water that will undergo the valence change. At the anode the water will oxidize as follows: $2(H^+ + OH^-) \rightarrow 4H^+ + O_2$ with the production of oxygen and local decrease in pH. Conversely at the cathode the water will reduce $2(H^+ + OH^-) \rightarrow H_2 + 2(OH^-)$ to bubble hydrogen and locally increase the pH.

This effect is commonly observed for iontophoresis applications using inert or passivated electrodes such as stainless steel, graphite, platinum (Pt) or gold (Au). In such cases, the runaway pH change has the potential to cause mild to severe irritation, inhibit the drift of the cations or anions into the epidermis (since it alters the conductivity and permeability of the skin), and degrade the formulation. In contrast, this effect is less pronounced when using poor electrolytes such as oil-in-water emulsions.

Reactive Electrodes: Silver/Silver Chloride Electrodes

Figure 10:
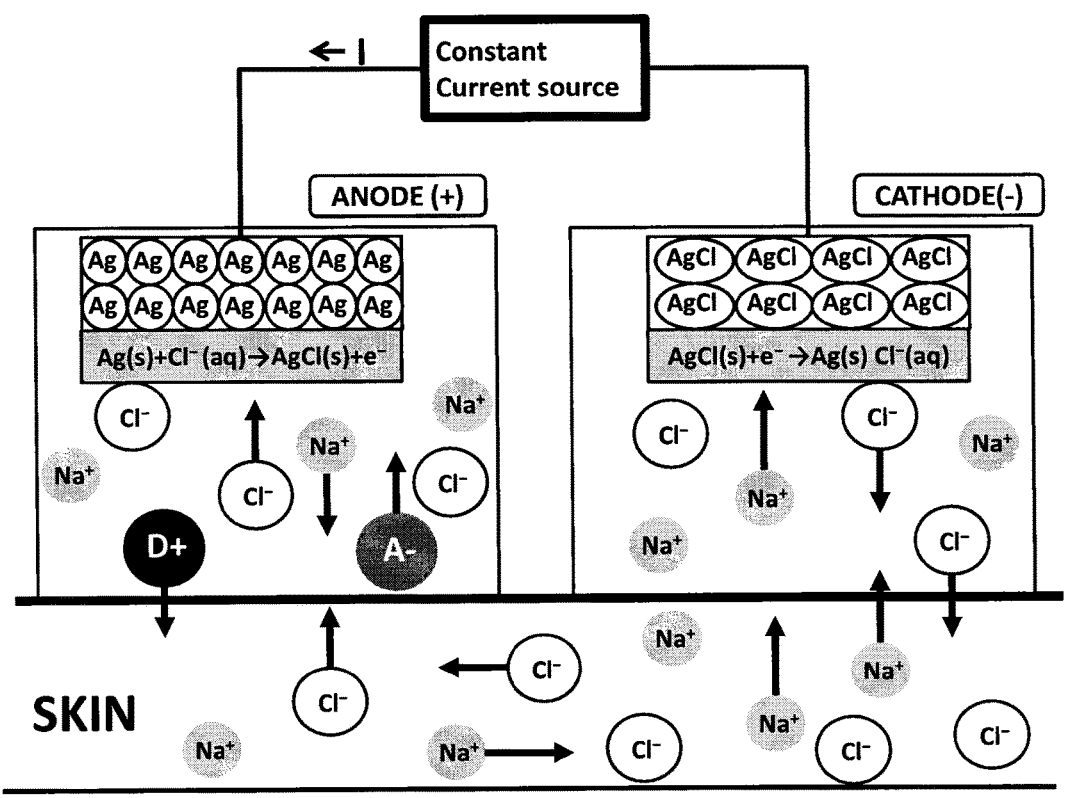
FIG. 10 is a diagram demonstrating use of chloride for anion flux pictorially.

In order to alleviate the redox of water that occurs at inert electrodes—and the concomitant pH related irritation—a use of a sacrificial electrode offers a safe and cost effective solution. A mainstay for reactive/sacrificial electrodes has been the medically benign silver/silver chloride (Ag/AgCl) electrode. This surface includes of a mixture of Ag metal particles and AgCl salts particles and can serve as both a sacrificial anode or cathode. If used as an anode, the Ag particles oxidize ($Ag^\circ \rightarrow Ag^+ + e^-$) and if used as a cathode, the AgCl reduces ($Ag^+ + e^- \rightarrow Ag^\circ$). The significance of the chloride anion in this case is that in either the reduction or oxidation reaction it becomes parts of an overall chloride ($Cl^-$) flux. This flux is due to chloride anions supplied in the formulation (as contained buffered saline solutions) as well as subcutaneous electrolytes. The use of chloride for anion flux is common for many iontophoresis prescriptions and can be sourced within the formulation (e.g. phosphate buffered saline). FIG. 10 is a diagram demonstrating use of chloride for anion flux pictorially—which presents the equivalent scenario of a pure Ag anode and pure AgCl cathode.

Most iontophoretic formulations have an ion and a counter ion ($D^+A^-$). Here the electron donor ($D^+$) is targeted for percutaneous infusion. The Ag of the Ag/AgCl electrode surface acts as the oxidizing species whereby it draws the counter ion acceptor ($A^-$) and binds with chloride (left side of the diagram in FIG. 10). If another Ag/AgCl surface is used as the counter electrode its AgCl will reduce to Ag metal and release chloride anions. Not demonstrated in FIG. 10 is the converse (an equally applicable) situation whereby the acceptor ($A^-$) is the ion which is required to be infused. In this situation, the active $D^+A^-$ would reside at the cathode side compartment. The Ag/AgCl electrode system is a very prevalent and compelling option as far as reactive electrodes but as with any reactive electrode care must be taken not to install chemistry that allows metal ion infusion.

Silver/silver chloride electrodes can be produced by a variety of methods. One common method is the immersion of a Ag metal finished surface into HCl and/or KCl and the application of current. Thin mixed electrodes such as this, are common consumables in medical iontophoresis.

Reactive Electrodes: Intercalation Electrodes

Other reactive electrodes have indeed been utilized which offer alternatives to Ag/AgCl. Another effective way to accommodate valence changes and control pH of iontophoresis treatments is to take advantage of the intercalation of $Li^+$, $Na^+$, and $K^+$ into a variety of matrices. In this scenario, these alkali metals induce partial valence states in materials such as: graphite, multi-valence metal oxides (of V, Fe, Mn, Mo, W) and intrinsically conductive polymers (polypyrrole, polyvinylcarbazole, polythiophene, etc).

Such is the working principle for Li-Ion batteries whereby $Li^+$ exists in different valence environments between carbon and metal oxide electrodes. With intercalation electrodes, the alkali ion is the mobile species responsible for the valence changes—in that they can reduce upon entry and oxidize upon exit. If M represents the alkali and A the matrix, the reversible half reactions are: $Mx+y\ Y \leftrightarrows xM^+ + MyA + e^-$. This solution is attractive if a given formulation will not accommodate Cr or other anions for Ag/AgCl—but will allow an alkali ion flux.

Formulation-Specific Electrodes

Since much variability can exist with any potential iontophoresis electrode and formulation combination, it will be advantageous to have a platform whereby a given formulation will also make provision for an appropriate electrode surface to be used in combination. Therefore, the appliance 100 preferably includes each embedded electrode 130 having an electrochemically appropriate surface for the treatment area 81 with respect to the application, the skin or circuit contact (e.g. hand, wrist, adjacent areas, etc.), and the corresponding active formulation. An electrochemically appropriate surface is one in which the ionic current comes from consumption of a layer on a surface of the embedded electrode 130.

Figure 4A:
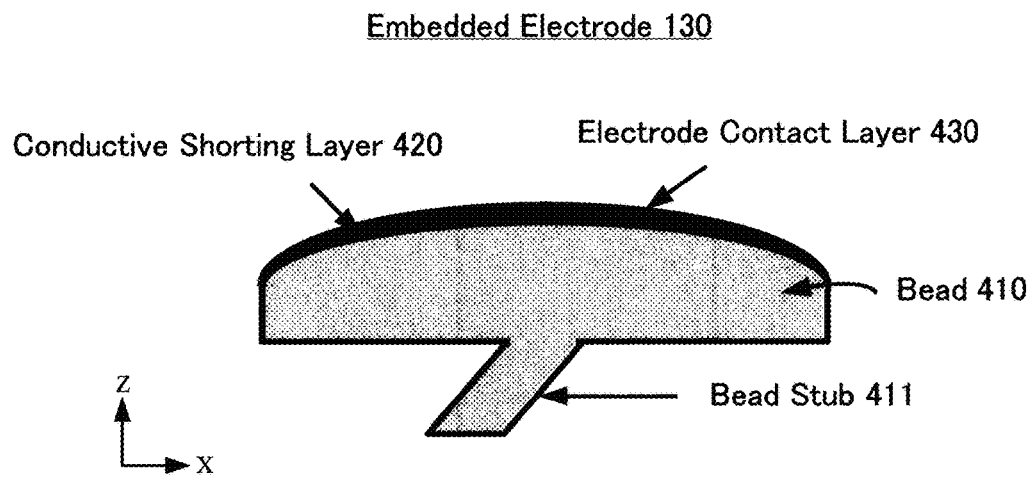
FIG. 4A shows a schematic illustration of a cross-sectional view of the embedded electrode according to an embodiment.

FIG. 4A shows a schematic illustration of a cross-sectional view of the embedded electrode 130 or formulation-specific electrode according to an embodiment. The embedded electrode 130 is shown having an electrode support portion or a bead 410 coated with a conductive shorting layer 420 and an electrode contact layer 430. A bead stub 411 is shown extending from the bead 410 as both a mechanical and electrical connector to the end effector 120. The bead stub 411 can have many different shapes including having either male or female features. In one example, bead stub 411 can be designed to attach to the arm 122 of the end effector 120 such that the embedded electrode 130 can be positioned at different distances along the arm 122, thereby changing the center of mass of the arm 122.

The bead 410 can be made from a low cost and disposable plastic or any commodity polymer material. The bead's outer surface is layered with the conductive shorting layer 420 such as a thin layer of electrochemically compatible metal, salt, compound, or polymer. The conductive shorting layer 420 allows contact with external circuitry such as the electrical system 200 and also serves to promote adhesion of the electrode contact surface layer 430. The electrode contact surface layer 430 is made of an appropriate formulation-specific material. In one example the electrode contact surface layer 430 is Trivalent Chromium.

A number of deposition processes are available in order to coat the bead 410 surface with the desired electrical shorting/adhesion layer and the formulation-specific electrode materials including: thermal and e-beam evaporation deposition, sputtering, electroplating, electroless plating, stencil and screen printing, ink-jet printing, plasma and powder spray coating, dip coating, spin casting, doctor blading, additive and 3-D printing.

In one embodiment the electrode contact layer 430 can be a disposable adhesive membrane that can applied by the subject.

In another embodiment, the embedded electrodes 130 can be replaceable and include a reservoir of the corresponding formulation such that the formulation and the electrode contact surface layer 430 are entirely consumed with a similar timing.

Figure 4B:
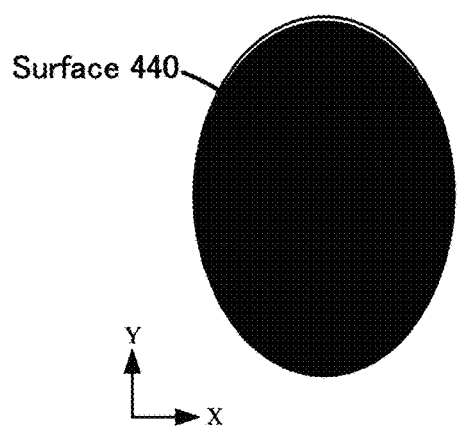
FIG. 4B shows a schematic of a top view of a surface of the embedded electrode having uniform coloring according to an embodiment.

FIG. 4B shows a schematic of a top view of a surface 440 of the embedded electrode 130 having uniform coloring according to an embodiment. In this example, the embedded electrode 130 is shown with only the electrode contact layer 430 exposed.

Figure 4C:
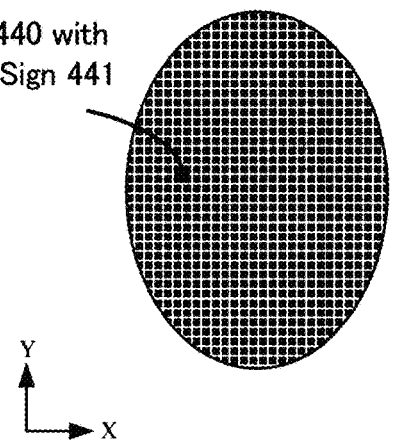
FIG. 4C shows a schematic of a top view of the surface of the embedded electrode having an indicator pattern according to an embodiment.

FIG. 4C shows a schematic of a top view of the surface 440 of the embedded electrode 130 having an indicator sign 441 according to an embodiment. In one example, the indicator sign 441 can be configured to indicate that the conductive shorting layer 420 is exposed through the electrode contact layer 430. In another example, the indicator sign 441 can be configured to indicate that the electrode contact layer 430 is consumed or compromised. In another example, the indicator sign 441 can be configured to indicate that the electrode contact layer 430 is not optimal for the formulation used. The indicator sign 441 can be a pattern, a color, or any other type of indication.

Figure 4D:
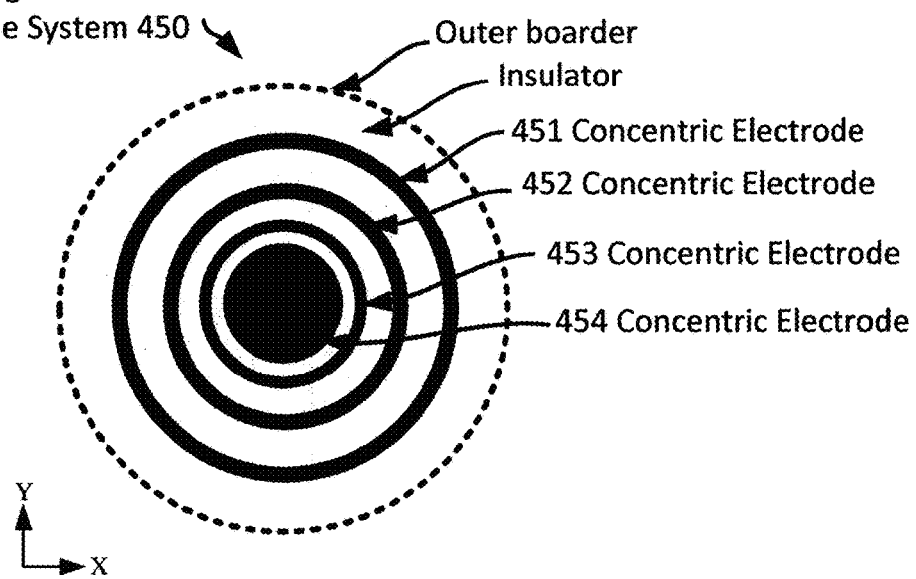
FIG. 4D shows an embodiment of the embedded electrode divided into multiple concentric electrodes.

FIG. 4D shows an embodiment of the embedded electrode 130 divided into multiple concentric electrodes forming a concentric electrode system 450. Each concentric electrode can be separated from the other concentric electrodes by an insulator. In an aspect each concentric electrode in the concentric electrode system 450 can be configured to be separately and individually in communication with the electrical system 200 and thereby independently controlled.

In one example, the concentric electrode system 450 can be made from an electrode support portion 410 having a set of interlaced conductive shorting layers 420 and a set of electrically insulating layers disposed over a surface of the electrode support portion 410, and an electrode contact layer 430 disposed over a surface of the set of conductive shorting layers 420. Here the electrode support portion 410 is configured to function as a mechanical coupler and as a multiple electrical connector to the set of conductive shorting layers 420 such that each conductive shorting layer is electrically isolated from the other layers.

In the example shown in FIG. 4D, the concentric electrode system 450 is divided into four concentric electrodes 451, 452, 453, and 454 where the two outermost concentric electrodes 451, 452 can be used to drive a voltage, the second concentric electrode from the center 453 can be used as a guard electrode, and the center concentric electrode 454 can be used as a current sink or the ground electrode. As used here, the guard electrode acts to divert or sink a current flow along the skin that could lead to a hot spot. By using the guard electrode, current is forced to follow a deeper path through the skin tissue. In an aspect, the concentric electrode system 450 can be used for performing multifrequency electrical impedance such as in "P. Åberg, I. Nicander, J. Hansson, P. Geladi, U. Holmgren, and S. Ollmar, Skin Cancer Identification Using Multifrequency Electrical Impedance—A Potential Screening Tool, IEEE Transactions on Biomedical Engineering, Vol. 51, No. 12, December 2004," herein incorporated by reference.

In an aspect the concentric electrode system 450 can be configured to be used in the diagnostic mode for sensing or monitoring any of the parameters of the skin or biomarkers in one or more depths of the skin layers.

Figure 5A:
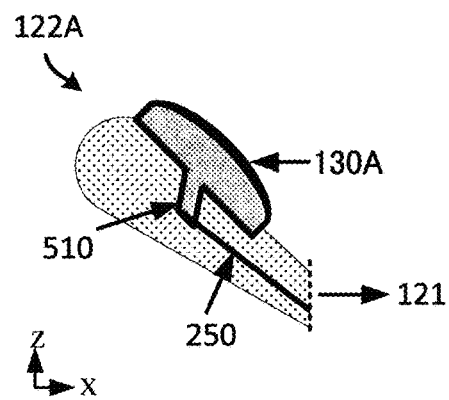
FIGS. 5A-B show schematic illustrations of a cross-section of an arm of a representative end effector in accordance with the disclosed embodiments.
Figure 5B:
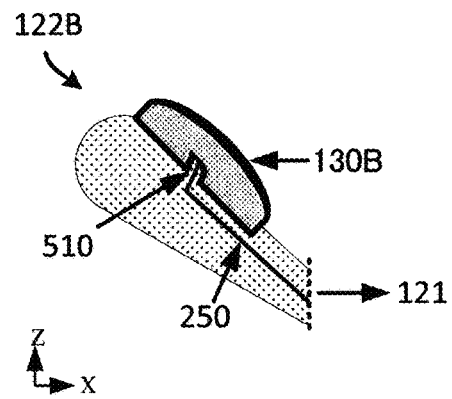

FIG. 5A shows a schematic illustration of a cross-section of an arm 122A of a representative end effector 120 in accordance with the disclosed embodiment in FIG. 3B. The arm 122A is shown having at least one embedded electrode 130 and electrical wiring 250 configured to communicate with the electrical system 200. The arm 122 can have one or more complementary attachment features 510 for both electrical and mechanical connection to the embedded electrode 130. As shown here the attachment feature 510 has a female receiving shape. FIG. 5B shows a schematic illustration of a cross-section of an arm 122B of a representative end effector 120 in accordance with the disclosed embodiment in FIG. 3B, where the arm 122B includes an attachment feature 510 having a male receiving shape.

In one aspect, each arm 122 is considered an extension of the central portion 121 of the end effector 120 and can be composed of the same set of materials. As an extension from the central portion 121, each arm 122 can have a mechanical center of mass and a moment of inertia similar to a cantilever beam or a pendulum. The moment of inertia of each arm 122 can be designed by several ways such as changing a dimension (e.g. length, width, thickness, and uniformity) of the arm 122, hardness (e.g. Young's modulus of materials used, stiffeners), or connection design to the end effector 120 (e.g. webbing, tapering, filleting).

In one aspect, the moment of inertia of each arm 122 can be tailored to the frequency of the mechanical motion of the device head 110 and the mechanobiology stimuli. In one aspect, the mechanical motion of the device head 110 can be designed such that it operates at one or more harmonic frequencies based on the moment of inertia of each arm 122.

In one embodiment, the moment of inertia of each arm 122 can be varied by modifying its center of mass. The center of mass of the arm 122 can be modified according to several scenarios. In one example, the embedded electrodes 130 can have different densities such that an embedded electrode 130 with a differing weight changes the center of mass of the arm 122. In another example, the embedded electrode 130 can be placed at different positions along the arm 122, thereby changing the center of mass of the arm 122.

In an aspect, the end effector 120 can include a plurality of embedded electrodes 130 that interact with a region of skin on the face. Having multiple embedded electrodes 130 on the arm 122 can be unique for the different functional modes, such as the diagnostic mode.

Figure 5C:
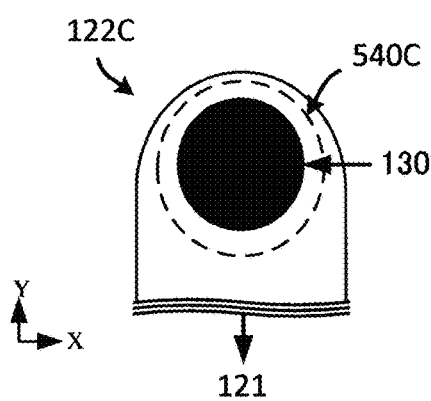
FIGS. 5C-E show schematic illustrations of a top view of different examples of embedded electrodes on the arm in accordance with the disclosed embodiments.
Figure 5D:
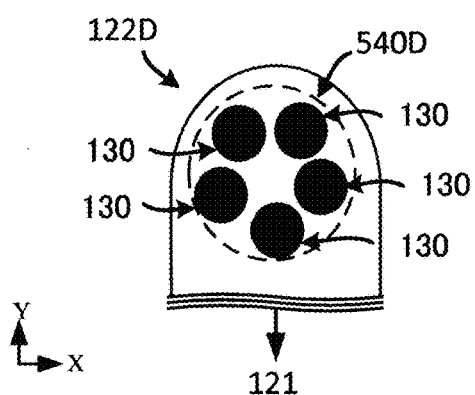
Figure 5E:
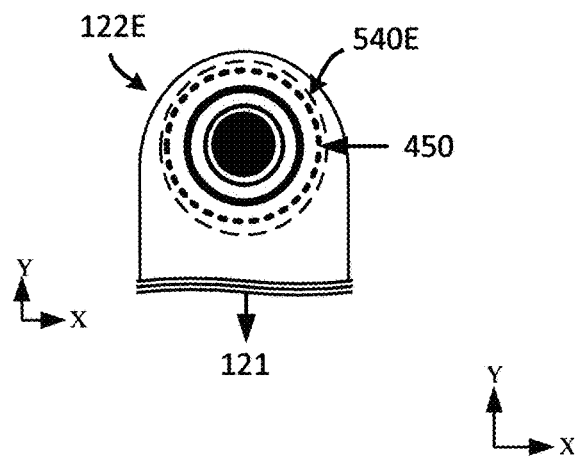

FIGS. 5C-E show schematic illustrations of a top view of different examples of embedded electrodes on the arm 122C-E in accordance with the disclosed embodiments. FIG. 5C shows a schematic illustration of a top view of the arm 122C having a single embedded electrode 130 resulting in an arm electrode assembly 540. The arm electrode assembly 540 reflects a spatial distribution of the one or more embedded electrodes 130. FIG. 5D shows a schematic illustration of a top view of the arm 122D having a plurality of embedded electrodes 130 arranged in an arm electrode assembly 540D. FIG. 5E shows a schematic illustration of a top view of the arm 122E including the concentric electrode system 450 resulting in an arm electrode assembly 540E. In addition, many other variations on the number and arrangement of the embedded electrodes 130 on either the arm 122 or the central portion 121 are possible.

Figure 6A:
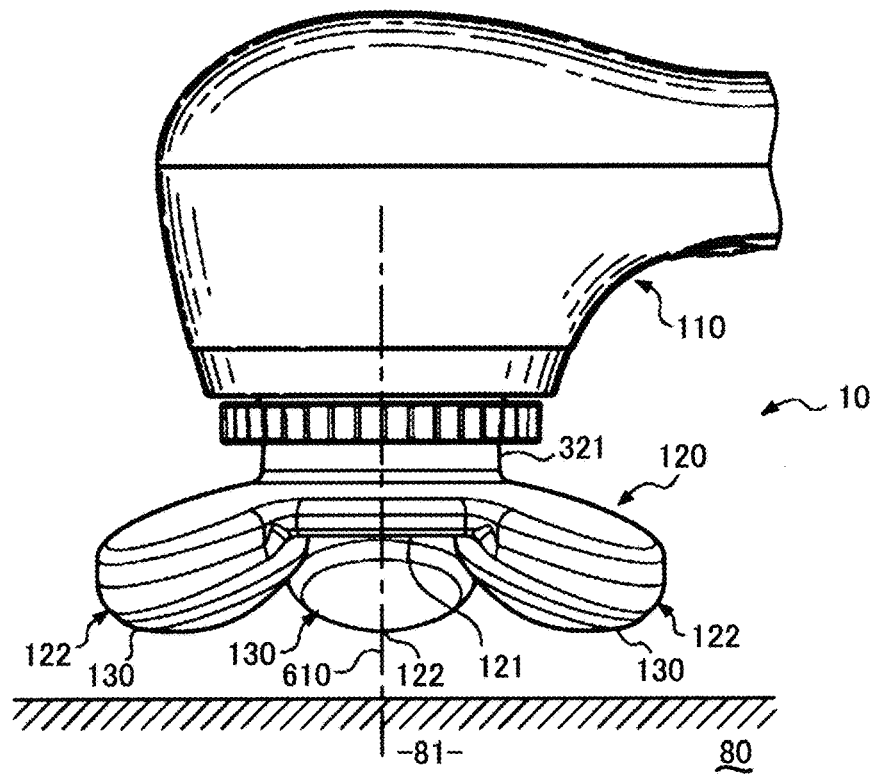
FIGS. 6A and 6B depict, respectively, an unloaded condition and a loaded condition of the system against a portion of the skin or the treatment area.
Figure 6B:
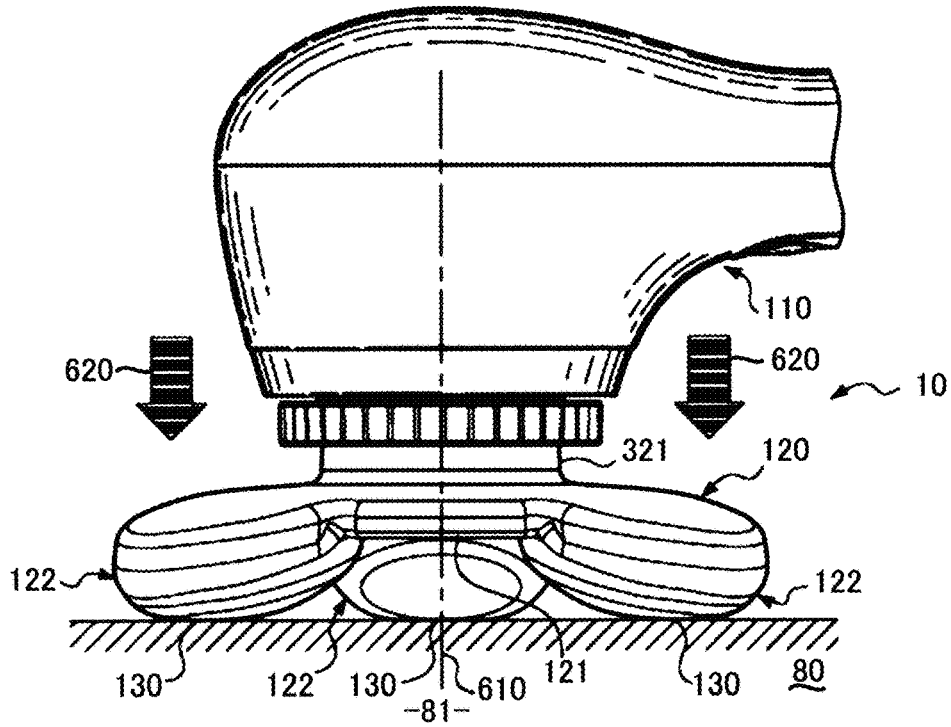

FIGS. 6A and 6B depict, respectively, an unloaded condition and a loaded condition of the system 10 against a portion of the skin 80 or the treatment area 81. The system includes an appliance 110 coupled to an end effector 120. The end effector 120 includes a plurality of embedded electrodes 130. In one embodiment, the plurality of embedded electrodes 130 are located a distance from each other based on an inverse of a motion frequency. Each of the plurality of embedded electrodes 130 is located on one of a plurality of arms 122. The end effector has a central portion 121 located between the plurality of arms 122. The end effector 120 is coupled to the appliance 110 via a central support 321 that is located opposite of the central portion 121. The portions of the end effector 120 that include the arms 122 are cantilevered out away from the central support 321.

In the embodiment shown in FIG. 6A, the system 10 is in an unloaded state (i.e., the end effector 120 is not in contact with the portion of the skin 80). The appliance includes a motor that moves the end effector 120. In one embodiment, the motor imparts oscillating movements to the end effector 120 about an axis 610. When the motor is operating, the system 10 has a resonant frequency based on a desired motion frequency. In one embodiment, the motion frequency is selected based on an anti-aging effect stimulated by a cyclical stimulus within the portion of skin at the motion frequency. As shown in FIG. 6A, the end effector 120 has a cupped shape where the embedded electrodes 130 are located closer to the treatment area 81 than the central portion 121. From the point shown in FIG. 6A, as the system 10 is lowered to the treatment area 81, the embedded electrodes 130 are the first portions of the system 10 to contact the portion of the skin 80.

In the embodiment shown in FIG. 6B, a force 620 is applied to the system 10 to bias the end effector 120 toward the portion of the skin 80 or the treatment area 81. In one embodiment, the force 620 applied to the system 10 is in a range from about 85 grams-force (approximately 0.83 N) to about 100 grams-force (approximately 0.98 N). In the embodiment shown in FIG. 6B, the force 620 applied to the system 10 causes the cantilevered portions of the end effector 120 to deflect toward the appliance 110. Such a deflection of the cantilevered portions is possible, in some examples, because the cantilevered portions of the end effector 120 are made of a non-rigid material. While the deflection of the cantilevered portions of the end effector 120 may modify the cup shape of the end effector 120, the force 620 does not cause the central portion 121 to touch the treatment area 81. Thus, only the arms 122 remain in contact with the treatment area 81 when the force 620 is applied. Any contact of the end effector 120 with the treatment area 81, other than the contact between the arms 122 and the end effector 120, may disrupt any cyclical stimulus of the treatment area 81 by the end effector 120.

With the force 620 applied to the system 10, the operating motor of the appliance 110 continues to move the end effector 120. The movement of the end effector 120 when the force 620 is applied to the system 10 produces a cyclical stimulus within the treatment area 81 at about the motion frequency. In one example, the cyclical stimulus is a wave-based mechanical strain that propagates through the treatment area 81. The location of the plurality of embedded electrodes 130 (i.e., at a distance from each other based on an inverse of a motion frequency) encourages propagation of the cyclical stimulus because the cyclical stimulus created by each of the plurality of embedded electrodes 130 is in phase with the other(s) of the plurality of embedded electrodes 130. In other words, one of the plurality of embedded electrodes 130 does not cancel out the cyclical stimulus created by another one of the plurality of embedded electrodes 130.

Figure 6C:
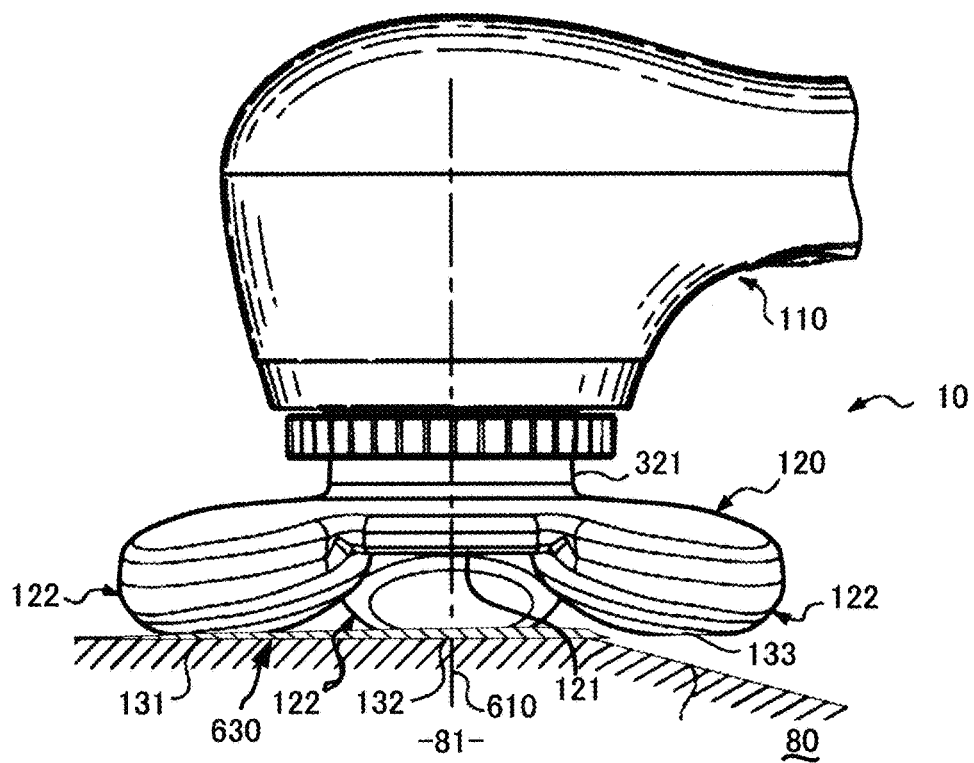
FIG. 6C depicts a loaded condition of the system against a portion of the skin or the treatment area where at least one embedded electrode is not in contact with the skin.

In the embodiment shown in FIG. 6C, the system 10 is shown with at least one arm 122 on the end effector 120 not being in contact with the portion of the skin 80 or the treatment area 81. Here the end effector 120 is shown with three embedded electrodes 131, 132, and 133. As compared to FIG. 6B, the skin 80 is shown having a contour such that there is a large separation with the embedded electrode 133. The embedded electrodes 131 and 132 are in contact with the skin 80 while the embedded electrode 133 is shown away from the skin 80 and no longer in electrical communication with the skin 80. In one case, the embedded electrode 133 is supplied with power similar as the embedded electrodes 131 and 132 that are in contact with the skin 80.

In order to use the device, the subject can place the electrode assembly 140 over the treatment area 81, after optionally having deposited the formulation 630 on the skin 80 or on the embedded electrodes 130. In another case, the electrical system 200 can detect that the embedded electrode 133 is not sufficiently in contact with the skin 80 and stop supplying power to the embedded electrode 133.

Figure 6D:
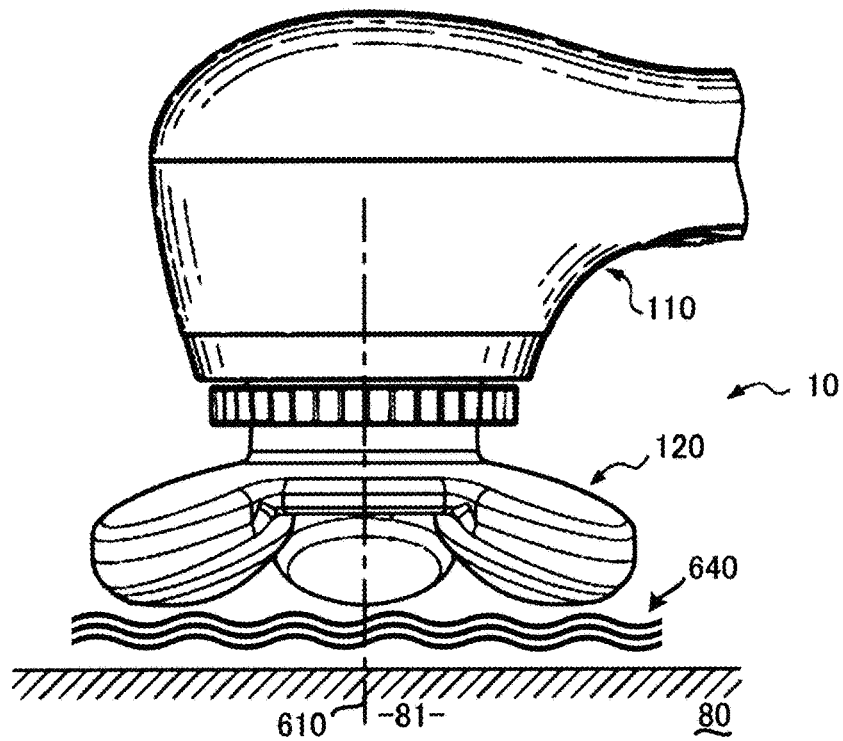
FIG. 6D shows the system operating in a heating mode with heat waves radiating toward the skin.

FIG. 6D shows the system 10 operating in the heating mode with heat waves 640 radiating toward the skin 80 and the treatment area 81. The heat therapy mode can be configured to provide heat therapy, to enhance the infusion of actives or the removal of impurities, and to deliver a pleasurable experience. Accordingly the appliance 100 advantageously includes the heating element. The heating element can be any source of heat to provide heat waves 640 and may include a heating resistor or a thermoelectric element or an infrared source. Preferably, the heating element includes an infrared source or a resistor. In an aspect the heating element can modify the temperature of an external surface of the end effector 120 and/or of the treatment area 81 and/or to transmit energy to the external surface of the end effector 120 and/or to the treatment area 81.

The appliance 100 may include a heating module which can be configured to control the heating of the external surface of the end effector 120 to a predefined temperature, for example to a temperature of between 35° C. and 45° C. In the case where the appliance 100 includes the heating module, the heating surface can reach a temperature of 10° C. to 35° C. greater than room temperature, preferably of 15° C. to 25° C. greater in the heating mode.

The power delivered by the heating module may be between 0.25 and 10 W, preferably between 0.5 and 5 W. More preferably, the heating element is housed entirely inside the device head 110. The resistor may be connected to the electrical system 200 by two insulated connectors, using for example the location of the sensors 260. The infrared source may be integrated into the device head 110 or the handle 112.

An external part of the appliance 100, for example a shell, can serve to guide the infrared radiation towards the end effector 120. The electrical system 200 may include at least one button 111 which is connected in series with the heating element and is configured to modify the power to the heating element and to control the amount of heat.

Interaction between arms of an end effector 120 and portions of skin is affected by more than just the location of the arms. FIGS. 7A through 7F depict embodiments of arms 122 and examples of results of the embodiments of arms on skin displacement. The arms 122 depicted in FIGS. 7A through 7F are capable of being used with embodiments of end effectors 120 described here. In addition, the arms of an end effector are usable to apply treatment compositions to a portion of skin.

Figure 7A:
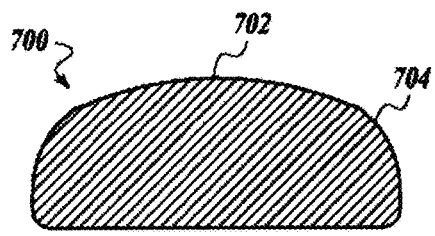
FIGS. 7A through 7H depict embodiments of arms and examples of results of the embodiments of the arms on skin displacement.

FIG. 7A depicts a side view of an embodiment of a contact area 700. The contact area includes a smooth face 702 and a rounded shoulder 704. In some embodiments, with used in an end effector with a plurality of arms, the smooth face 702 includes a contact location that is configured to contact a portion of skin. The rounded shoulder 704 has a radius that does not provide a noticeable edge to the face 702.

Figure 7B:
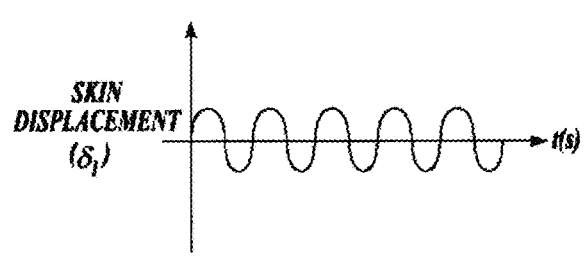

FIG. 7B depicts a chart showing an example of skin displacement $\delta_1$ of a portion of skin over time when the portion of skin is in contact with the contact area 700 and the contact area 700 produces a cyclical stimulus within the portion of skin.

Figure 7C:
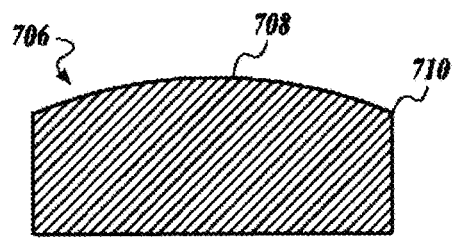
Figure 7D:
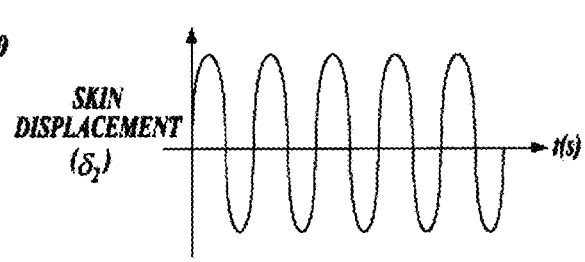

FIG. 7C depicts a side view of an embodiment of a contact area 706. The contact area includes a smooth face 708 and a rounded shoulder 710. In some embodiments, when used in an end effector with a plurality of arms, the smooth face 708 includes a contact location that is configured to contact a portion of skin. The rounded shoulder 710 has a radius that provides a noticeable edge to the face 708. In the embodiments shown in FIGS. 7A and 7C, the radius of the rounded shoulder 710 is less than the radius of the rounded shoulder 704. FIG. 7D depicts a chart showing an example of skin displacement $\delta_2$ of a portion of skin over time when the portion of skin is in contact with the contact area 706 and the contact area 706 produces a cyclical stimulus within the portion of skin.

Comparing the charts in FIGS. 7B and 7D, the cyclical stimuli shown have the same frequency, but the skin displacement $\delta_2$ using the rounded shoulder 710 on the contact area 706 is greater than the skin displacement $\delta_1$ using the rounded shoulder 704 on the contact area 700. The greater skin displacement $\delta_2$ is due to the greater friction between the portion of skin and the noticeable edge provided by the rounded shoulder 710 on the face 708.

Figure 7E:
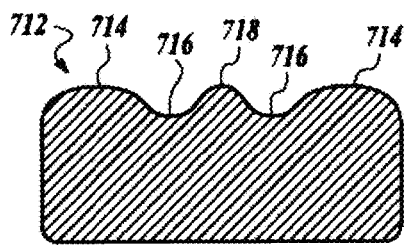
Figure 7F:
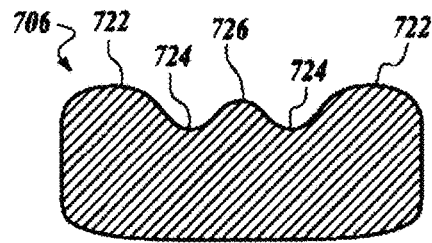

FIGS. 7E and 7F depict cross-sectional views of two embodiments of arms with slits across faces of the arms. FIG. 7E depicts a cross-sectional view of a contact area 712 that has a face 714. The contact area 712 also has two slits 716 across the face 714. While the embodiment of contact area 712 has two slits, in other embodiments, arms have other numbers of slits, such as one slit across the face. Between the two slits 716, a portion 718 of the contact area 712 returns back to approximately the same level of the face 714. The recesses in the face 714 created by the slits 716 are capable of containing treatment composition as the contact area 712 is moved across a portion of skin. In this way, the recesses in the face 714 created by the slits 716 function as a small reservoir to more evenly spread treatment composition across a portion of skin. The slits 716 also provide distinct edges on the face 714 that provide greater friction between the contact area 712 and the portion of skin to cause greater skin displacement in the portion of skin.

FIG. 7F depicts a cross-sectional view of a contact area 720 that has a face 722. The contact area 720 also has two slits 724 across the face 722. While the embodiment of contact area 722 has two slits, in other embodiments, arms have other numbers of slits, such as one slit across the face. Between the two slits 724, a portion 726 of the contact area 720 is raised above the deepest parts of the two slits 724, but is recessed back from the level of the face 722. The recess in the face 722 created by the slits 724 and the recessed portion 726 is capable of containing treatment composition as the contact area 720 is moved across a portion of skin. In this way, the recess in the face 722 created by the slits 724 and the recessed portion 726 functions as a small reservoir to more evenly spread treatment composition across a portion of skin. The recess in the face 722 created by the slits 724 and the recessed portion 726 also provides friction between the contact area 720 and the portion of skin to cause greater skin displacement in the portion of skin.

Figure 7G:
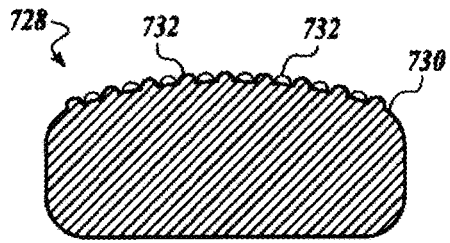
Figure 7H:
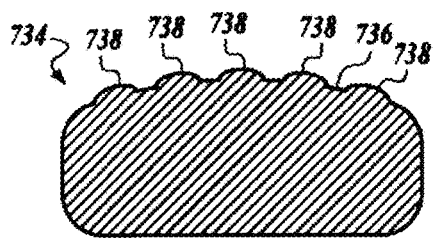

FIGS. 7G and 7H depict side views of embodiments of arms with surface texturing on their faces. FIG. 7G depicts a side view of a contact area 728. The contact area 728 includes a face 730 with surface texturing in the form of dimples 732 on the face 730. FIG. 7H depicts a side view of a contact area 734. The contact area 734 includes a face 736 with surface texturing in the form of linear bumps 738 on the face 736. In other embodiments, other forms of surface texturing are used on the faces of arms. Examples of the benefits of surface texturing on the face of a contact area include one or more of better application of treatment composition into a portion of skin, greater skin displacement by the contact area, or improved sensation of the operation of the contact area against the portion of skin.

FIGS. 8A through 8D depict top views of embodiments of end effectors 120 with different shapes of the central portion 121, different numbers and arrangements of the arms 122, and different numbers and arrangements of the embedded electrode 130. Each of FIGS. 8A through 8D depicts a top view of an end effector 120A-D resulting in a different electrode assembly 140. Each end effector 120A-D includes a plurality of embedded electrodes 130A-D. Each of the embedded electrodes 130A-D is located on one of a plurality of arms 122A-D. Each end effector 120A-D also includes a central portion 121A-D that is recessed away from the arms 122A-D such that the embedded electrodes 130A-D are the first portions of the end effectors 120A-D that would contact a portion of skin.

The end effectors 120A-D have different numbers and arrangements of arms 122A-D. More specifically, as depicted in FIG. 8A, the end effector 120A has a flower arrangement with a circular central portion 121A and six circular arms 122A around the circular central portion 121A. As depicted in FIG. 8B, the end effector 120B has an arrangement that is a variation of a flower arrangement. The end effector 120B has a circular central portion 121B and eight pointed arms 122B around the circular central portion 121B. The embedded electrode 130B is shown with a non-spherical shape. As depicted in FIG. 8C, the end effector 120C has a butterfly arrangement with a central portion 121C with a vesica piscis shape and four arms 122C. The four arms 122C are arranged with two sets of two arms 122C on each side of the central portion 121C. As depicted in FIG. 8D, the end effector 120D has a pie-shaped arrangement with a circular central portion 121B and six pie-piece-shaped arms 122D around the circular central portion 121D. Many other variations on the number and arrangement of arms 122 on an end effector 120 are possible.

Each of the embodiments of end effectors 120A-D depicted in FIGS. 8A through 8D include a plurality of embedded electrodes 130A-D. In one example, the embedded electrodes 130A-D are located at a target distance from each other that is based on an inverse of the motion frequency. It may not be possible to locate four or more embedded electrodes equidistantly from each other. For example, with four embedded electrodes located at corners of a square, an embedded electrode may be equidistantly located from the other embedded electrodes at neighboring corners, but will not be equidistantly located from the embedded electrode that is across the diagonal of the square. However, even if it may not be possible for four or more embedded electrodes to be located equidistantly from each other, four or more embedded electrodes may be located at a target distance from each other that is based on an inverse of the motion frequency. For example, the four or more embedded electrodes may be located at a target with respect to each other such that the individual ones of the four or more embedded electrodes do not cancel out cyclical stimulus generated by the others of the four or more embedded electrodes. In addition, many other variations on the number and arrangement of the embedded electrodes 130 on either the arm 122 or the central portion 121 are possible.

Figure 9A:
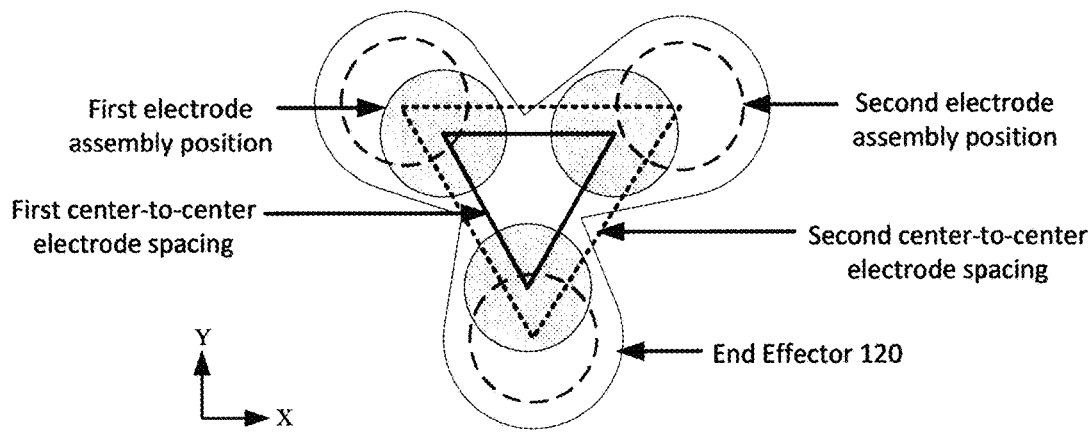
FIG. 9A shows an embodiment of the end effector that can be adjusted to change a spatial distribution of the electrode assembly.
Figure 9B:
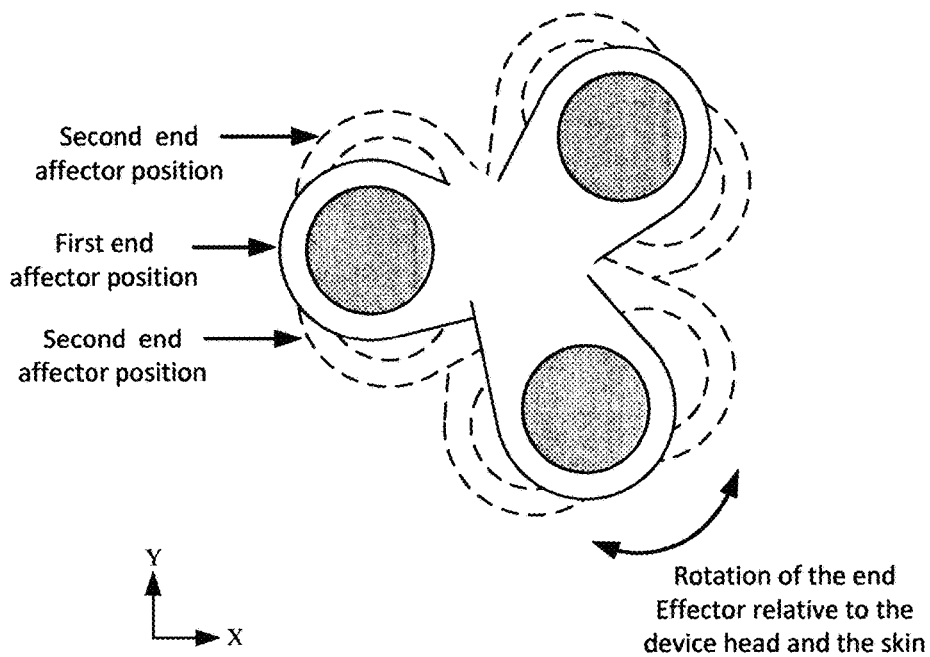
FIG. 9B shows a change in the end effector position relative to the skin due to a rotation of the end effector.

FIG. 9A shows an embodiment of the end effector 120 that can be adjusted to change the spatial distribution of the electrode assembly 140. FIG. 9B shows a change in the end effector 120 position relative to the skin due to a rotation of the end effector 120.

In an aspect, the electrical system 200 can be configured to coordinate the power supplied to the skin by the electrode assembly 140 with the oscillatory or reciprocating mechanical motion of the end effector 120. In an example of coordination includes alternating between the massage mode, the iontophoresis mode, and the microcurrent mode.

In an aspect, the alteration between modes is interlaced at a frequency such that the modes can be perceived by the subject to be simultaneous. In a further example, the polarity of each embedded electrode 130 can change in coordination with the interlaced modes. The polarity change can be done at the frequency or pattern of the mechanical motion, at a harmonic of that frequency or pattern, or a separate frequency or pattern.

In an embodiment, the oscillatory or reciprocating mechanical motion can result in the end effector 120 having different spatial distances between each embedded electrode 130 and/or different spatial locations on the subject's skin. In both of these cases, a distance between each embedded electrode 130 and a location on the subject's skin can be varied such that a different optimal voltage/current profile should be applied. In an example, the voltage or current profile can be configured to account for the spatial differences resulting due to the mechanical movement relative to the skin.

Obviously, numerous modifications and variations of the present invention are possible in light of the above teachings. It is therefore to be understood that within the scope of the appended claims, the invention may be practiced otherwise than as specifically described herein.

What is claimed is:

1. A system for stimulating a portion of skin, the system comprising:
   at least two electrodes;
   a motor and an electrical system, the electrical system including a power source; and
   an end effector operably coupled to the motor and the electrical system, the end effector having at least one embedded electrode, from the at least two electrodes, disposed and operably coupled to the electrical system at which the end effector is configured to be in electrical communication with the portion of skin,
   wherein the motor is configured to subject the end effector to repetitive movements while contacting the skin to provide mechanical stimulation to the skin,
   wherein the at least one embedded electrode is configured to serve as a source electrode and another of the at least two electrodes is configured to serve as a return electrode,
   wherein the power source is configured to bias the source electrode to the return electrode and form an electric field with the portion of skin,
   wherein the end effector further includes a set of contact points that are located at a target distance from each other that is based on an inverse of a target motion frequency of the repetitive movements of the end effector.

2. The system of claim 1,
   wherein the motor is configured to move the end effector such that, when the motor is operating, the motor and end effector have a resonant frequency based on the target motion frequency,
   wherein, when the motor is operating and a force is applied to the system to bias the end effector toward the portion of skin, the end effector produces a cyclical stimulus within the portion of skin at about the target motion frequency.

3. The system of claim 1, wherein the power source is configured to form an electric field that performs iontophoresis in the portion of skin.

4. The system of claim 3, wherein a formulation is used during iontophoresis that includes one or more of a cosmetic composition, a medical ointment, and a cleanser that is capable of being applied to a portion of skin.

5. The system of claim 1, wherein the power source is configured to form an electric field that creates a microcurrent in the portion of skin.

6. The system of claim 1, further comprising a heating element configured to radiate heat to the portion of skin.

7. The system of claim 1, where the at least one embedded electrode is connected to the end effector via a flexible arm.

8. The system of claim 1, wherein the return electrode is disposed in a handle of the system configured to be gripped by a user's hand.

9. The system of claim 1, wherein the return electrode is another embedded electrode included as part of the end effector.

10. A method, implemented by a system for stimulating a portion of skin, the system including at least two electrodes, a motor, an electrical system that includes a power source; and an end effector operably coupled to the motor and the electrical system, the end effector having at least one embedded electrode, from the at least two electrodes, disposed and operably coupled to the electrical system at which the end effector is configured to be in electrical communication with the portion of skin, the method comprising:
    subjecting the end effector to repetitive movements while contacting the skin to provide mechanical stimulation to the skin, wherein the at least one embedded electrode is configured to serve as a source electrode and another of the at least two electrodes is configured to serve as a return electrode; and
    biasing, by the power source, the source electrode to the return electrode and form an electric field with the portion of skin,
    wherein the end effector further includes a set of contact points that are located at a target distance from each other that is based on an inverse of a target motion frequency of the repetitive movements of the end effector.

11. The method of claim 10, wherein the method further includes
    moving the end effector such that, when the motor is operating, the motor and end effector have a resonant frequency based on the target motion frequency, wherein, when the motor is operating and a force is applied to the system, biasing the end effector toward the portion of skin, the end effector producing a cyclical stimulus within the portion of skin at about the target motion frequency.

12. The method of claim 10, further comprising forming an electric field that performs iontophoresis in the portion of skin.

13. The method of claim 12, wherein a formulation is used during iontophoresis that includes one or more of a cosmetic composition, a medical ointment, and a cleanser that is capable of being applied to a portion of skin.

14. The method of claim 10, further comprising forming an electric field that creates a microcurrent in the portion of skin.

* * * * *